US007189405B1

(12) United States Patent
Rice et al.

(10) Patent No.: US 7,189,405 B1
(45) Date of Patent: Mar. 13, 2007

(54) PEPTIDE MIMICS OF CONSERVED GONOCOCCAL EPITOPES AND METHODS AND COMPOSITIONS USING THEM

(76) Inventors: Peter A. Rice, 55 Norfolk Rd., Chestnut Hill, MA (US) 02467; Jutamas Ngampasutadol, 8 St. Paul St., Cambridge, MA (US) 02139; Sunita Gulati, 14 Wheeler St., Gloucester, MA (US) 01930

( * ) Notice: Subject to any disclaimer, the term of this patent is extended or adjusted under 35 U.S.C. 154(b) by 0 days.

(21) Appl. No.: 09/699,224

(22) Filed: Oct. 27, 2000

Related U.S. Application Data

(60) Provisional application No. 60/162,491, filed on Oct. 29, 1999.

(51) Int. Cl.
   A61K 39/02 (2006.01)
   A61K 39/385 (2006.01)
   A61K 38/00 (2006.01)
   C07K 1/00 (2006.01)

(52) U.S. Cl. .............. 424/249.1; 424/234.1; 424/190.1; 424/193.1; 514/2; 530/300; 530/825; 530/350

(58) Field of Classification Search ........... 530/300, 530/350, 825, 806, 810, 317, 329; 514/2; 424/131.1, 134.1, 137.1, 249.1, 190.1, 193.1, 424/184.1, 234.1
See application file for complete search history.

(56) References Cited

U.S. PATENT DOCUMENTS

| | | | | |
|---|---|---|---|---|
| 5,051,408 A | * | 9/1991 | Cooper | 514/54 |
| 5,476,784 A | * | 12/1995 | Rice et al. | 435/240.27 |
| 5,780,029 A | * | 7/1998 | Ferrone et al. | 424/131.1 |
| 5,888,509 A | * | 3/1999 | Rice et al. | 424/130.1 |
| 5,939,067 A | * | 8/1999 | Rice et al. | 424/131.1 |
| 6,048,527 A | * | 4/2000 | Granoff et al. | 424/150.1 |
| 6,074,641 A | * | 6/2000 | Rice et al. | 424/131.1 |
| 6,099,839 A | * | 8/2000 | Rice et al. | 424/131.1 |
| 6,479,639 B1 | * | 11/2002 | Metchetner et al. | 530/387.9 |
| 2003/0026764 A1 | * | 2/2003 | Griffiths | 424/9.34 |

FOREIGN PATENT DOCUMENTS

| | | | |
|---|---|---|---|
| WO | WO 85/04654 | * | 10/1985 |
| WO | WO 94/22479 | | 10/1994 |
| WO | WO 97/46582 | | 12/1997 |
| WO | WO 98/46645 | * | 10/1998 |
| WO | WO 99/11660 | | 3/1999 |
| WO | WO 99/40189 | | 8/1999 |

OTHER PUBLICATIONS

Tam J.P. In: Peptide Antigens: A Practical Approach. (Ed) C.B. Wisdom. IRL Press, Oxford University Press, New York, 1993, pp. 83-90.*
Ngampasutadol et al. In: Abstracts of the 11th International Pathogenic Neisseria Conference, Nice, France, 1998, p. 159.*
Clements. Infect. Immunol. 58: 1159-1166, 1990.*
Huang et al. Mol. Immunol. 31: 1191-1199, 1994.*
Tam. In: Peptide Antigens. A Practical Approach. (Ed) Wisdom G.B. IRL Press, Oxford University Press, New York, pp. 83-90, 1994.*
Ahearn, J. M., M. B. Fischer, D. Croix, S. Goerg, M. Ma, J. Xia, X. Zhou, R. G. Howard, T. L. Rothstein, and M. C. Carroll. 1996. Disruption of the Cr2 locus results in a reduction in B-1a cells and in an impaired B cell response to T-dependent antigen. Immunity 4:251.
Apicella, M.A., M.A.J. Westerink, S.A. Morse, H. Schneider, P.A. Rice and J.M. Griffiss. 1986. Bactericidal antibody response of normal human serum to the lipooligosaccharade *Neisseria gonorrhoeae*. *J. Infect. Dis.* 153:520-526.
Amon, R., M. Shapira and C.O. Jacob. 1983. Synthetic Vaccines. J. Immunol. Methods 61: 261-273.
Banerjee A., R. Wang, S. N. Uljon, P. A. Rice, and E. C. Gotschlich. 1998 Identification of the gene (*lgtG*) encoding the lipooligosaccharide β chain synthesizing glucosyl transferase from *Neisseria gonorrhoeae*. Proc. Natl. Acad. Sci. USA 95:10872.
Böttger, E. C., and D. Bitter-Suermann. 1987. Complement and the regulation of humoral immune responses. Immunol. Today 8:261.
Britigan, B.E., M.S. Cohen and P.F. Sparling. 1985. Gonococcal infection: a model of molecular pathogenesis. *N. Eng. J. Med.* 312:1683-1694.
Brodin, N.T., J. Dahmén, B. Nilsson, L. Messeter, S. Mårtenson, J. Heldrup, H.O. Sjögren and A. Lundblad. 1988. Monoclonal antibodies produced by immunization with neoglycoproteins containing Galα1→4β1→4Glcβ-O and Galα1→4β1→4GlcNAcβ-O residues: useful immunochemical and cytochemical reagents for blood group P antigens and a differentiation marker in Burkitt lymphoma and other B-cell malignancies. *Int. J. Cancer.* 42:185-194.
Brooks, G.F. and C.J. Lammel. 1989. Humoral immune response to gonococcal infection. *Clin. Micro. Rev.* 2:S5-S10.
Brossay, L. et al., "Idiotype and Anti-Anti-idiotype Antibodies to *Neisseria gonorrhoeae* Lipooligosaccharides with Bactericidal Activity but No Cross-Reactivity with Red Blood Cell Antigens", *J. Immunol.*, 151, pp. 234-243 (1993).
Burritt, J.B., C.W. Bond, K.W. Doss and A.J. Jesiatis. 1996. Filamentous phage display of oligopeptide libraries. Anal. Biochem. 338: 1-13.
CDC. 1991. Pelvic Inflammatory Disease: Guidelines for Prevention and Management. *MMWR* 40:1-25.
CDC. 1982. Sexually transmitted diseases treament guidelines. *MMWR* 31:37S-42S 375-425.
CDC. 1984. Chromosomally mediated resistant *Neisseria gonorrhoeae*-United States. *MMWR* 33:408-410.
CDC Website. 2000. http://www.cdc.gov/ncidod/dastlr/gcdir/Resist/gisp.html.
Cohen, I.R., D.S. Kellogg and L.C. Norins. 1969. Serum antibody response in experimental human gonorrhoeae: immunoglobulins G, A and M. Br. J. Ven. Dis. 45:325-327.

(Continued)

*Primary Examiner*—S. Devi
(74) *Attorney, Agent, or Firm*—Fish & Neave IP Group Ropes & Gray LLP

(57) ABSTRACT

The present invention relates to peptide mimics of a conserved gonococcal epitope of *Neisseria gonorrhoeae*, which epitope is not found on human blood group antigens. This invention also relates to methods and compositions using such peptide mimics for the prophylaxis of gonorrheal infections.

21 Claims, 13 Drawing Sheets

OTHER PUBLICATIONS

Croix, D. A., J. M. Ahearn, A. M. Rosengard, S. Han, G. Kelsoe, M. Ma, and M. C. Carroll. 1996. Antibody response to a T-dependent antigen requires B cell expression of complement receptors. J. Exp. Med. 183:1857.

Dempsey, P. W., M. E. D. Allison, S. Akkaraju, C. C. Goodnow, and D. T. Fearon. 1996 C3d of complement as a molecular adjuvant: Bridging innate and acquired immunity. Sciences 271: 348.

Densen, P., S. Gulati and P.A. Rice 1987. Specificity of antibodies against *Neisseria gonorrhoeae* that stimulate neutrophil chemotaxis. *J. Clin. Invest.* 80:78-87.

Fischer, M. B., M. Ma, S. Goerg, X. Zhou, J. Xia, X. Zhou, R. G. Howard, T. L. Rothstein, E. Kremmer, F. S. Rosen, and M. C. Carroll. 1996. Regulation of the B cell response to T-dependent antigens by classical Pathway complement. J. Immunol. 157:549.

Fohn, M.J., T.A. Mietzner, T.W. Hubbard, S.A. Morse and E.W. Hook III. 1987. Human immunoglobulin G antibody response to the major gonococcal iron-regulated protein. *Infect. Immun.* 55:3065-3069.

Glynn, A.A. and M.E. Ward. 1970. Nature and heterogeneity of the antigens of *Neisseria gonorrhoeae* involved in the serum bactericidal reaction. *Infect. Immun.* 2:162-168.

Gnehm, H.E., S.I. Pelton, S. Gulati and P.A. Rice. 1985. Characterization of antigens from nontypable *Haemophilus influenzas* recognized by human bactericidal antibodies. *J. Clin. Invest.* 75:1645-1658.

Griffiss, H.M., J.P. O'Brien, R. Yamasaki, G.D. Williams, P.A. Rice and H. Schneider. 1987. Physical heterogeneity iof Neisserial lipooligosaccharides reflects oligosaccharides that differ in apparent molecular weight, chemical composition, and antigenic expression. *Infect. Immun.* 55:1792-1800.

Gulati, S., D.P. McQuillen, J. Sharon, and P.A. Rice. 1996. Experimental Immunization with a Monoclonal Anti-Idiotope Antibody that Mimics the *Neisseria gonorrhoeae* Lipooligosaccharide Epitope 2C7. J. Infect. Dis. 174: 1238-48.

Gupta, R.K. and G.R. Siber. 1995. Adjuvants for human vaccines—current status, problems and future prospects. Vaccine 13: 1263-1276.

Gupta, R.K. and G.R. Siber. 1995. Method for quantitation of IgG subclass antibodies in mouse serum by enzyme-linked immunosorbent assay. J. Immunol. Methods 181: 75-81.

Horng, W.J., "Selective Enhancement of a Subpopulation of Anti-*Neisseria gonorhoeae* Antibodies in Rabbits Through a Reverse Stimulation by Anti-Idiotype Antibodies", *Fed. Amer. Soc. Exp. Biol., 69th Ann. Meet.*, Apr. 21-26, 1985 (Anaheim, California), Abstract No. 7502, p. 1694.

Jeme, N.K. 1974. Towards a network theory of the immune system. *Ann. Immun. Inst. Pasteur*. 125C:373-389.

Joiner, K.A., R. Scales, J.A. Warren, M.M. Frank and P.A. Rice. 1985. Mechanism of action of blocking immunoglobulin G for *Neisseria gonorrhoeae*. *Clin. Invest.* 76:1765-1772.

Kasper, D.L., P.A. Rice and W.M. McCormack. 1977. Bactericidal antibody in genital infection due to *Neisseria gonorrhoeae. J. Infect. Dis.* 135:243-251.

Kennedy, R.C., K. Adler-Storthe, R.D. Henkel, Y. Sanchez, J..L. Melnick nad G.R. Dreesman. 1983. Immune response to hepatitis B surface antigen: enhancement by prior injection of antibodies to the idiotype. Science 221:853-855.

Kennedy, R.C., J.W. Eichberg, R.E. Landford and G.R. Dressman. 1986. Anti-idiotypic vaccine for type B viral hepatitis in chimpanzees. *Science* 232:220-223.

Kennedy, R.C. et al., *BioTechniques*, 3, pp. 404-409 (1985).

Kieber-Emmons T. 1998. Peptide mimotopes of carbohydrate antigens. Immunol. Res. 17: 95-108.

Kieber-Emmons, T., R.E. Ward, S. Raychaudhuri, R. Rein, and H. Kohler. 1986. Rational design and application of idiotope vaccines. *Int. Rev. Immunol.* 1:1-26.

Kim, J.J., R.E. Mandrell, H. Zhen, M.A.J. Westerink, J.T. Poolman and J.M. Griffiss. 1988. Electromorphic characterization and description of conserved epitopes of the lipooligosaccharides of group A *Neisseria meningitidis*. *Infect. Immun.* 56:2631-2638.

Klaus G.G.B., and J. H. Humphrey. 1977. The generation of memory cells I. The role of C3 in the generation of B memory cells. Immunology 33:31.

Lambden, P.R., J.E. Heckels, H. McBride and P.J. Watt. 1981. The identification and isolation of novel pilus types produced by variants of *Neisseria gonorrhoeae* P9 following selection in vivo. *FEMS. Microbiol. Lett.* 10:339-341.

Lammel, C.J., R.L. Sweet, P.A. Rice, J.S. Knapp, G.K. Schoolnik, D.C. Heilbron and G.F. Brooks. 1985. Antibody-antigen specificity in the immune response to infection with *Neisseria gonorrhoeae. J. Infect. Dis.* 152:990-1001.

Lowell, G.H., W.R. Ballou, L.F. Smith, R.A. Wirtz, W.D. Zollinger and W.T. Hockmeyer. 1988. Proteosome-lipopeptide vaccines: enhancement of immunogenicity for malaria CS peptides. Science 240: 800-802.

Luo P., M. Agadjanyan, J. Qiu, M.A. Westerink, Z. Steplewski and T. Kieber-Emmons. 1998. Antigenic and immunological mimicry of peptide mimotopes of Lewis carbohydrate antigens. Mol. Immunol. 35: 865-879.

Mandrell, R.E., H. Schneider, M.A. Apicella, W.D. Zollinger, P.A. Rice and J.M. Griffiss. 1986. Antigenic and physical diversity of *Neisseria gonorrhoeae* lipooligosaccharides. *Infect. Immun.* 54:63-69.

Mandrell, R.E., J.M. Griffiss and B.E. Macher. 1988. Lipooigosaccharides (LOS) of *Neisseria gonorrhoeae* and *Neisseria meningitidis* have components that are immunochemically similar to precursors of human blood group antigens: carbohydrate sequence specificity of the mouse monoclonal antibodies that recognize crossreacting antigens on LOS and human erythrocytes. *J. Exp. Med.* 168:107-126.

Mandrell, R.E. 1992. Further antigenic similarities of *Neisseria gonorrhoeae* lipooligosaccharides and human glycosphingolipids. *Infect. Immun.* 60:3017-3020.

McQuillen D. P., S. Gulati, and P. A. Rice. 1994. Complement-mediated bacterial killing assays. Methods Enzymol. 236: 137.

Molina, H., V. M. Holers, B. Li, Y.-F. Fang, S. Mariathasan, J. Goellner, J. Strauss-Schoenberger, R. W. Karr, and D. D. Chaplin. 1996. Markedly impaired humoral response in mice deficient in complement receptors 1 and 2. Proc. Natl. Acad. Sci. USA 93 :3357.

Morse, S.A., S. Stein and J. Hines. 1974. Glucose metabolism in *Neisseria gonorrhoeae*. *J. Bact.* 120:702-714.

Newhall, W.J., W.D. Sawyer, and R.A. Haak. 1980. Cross-linking analysis of the outer membrane proteins of *Neisseria gonorrhoeae*. *Infect. and Immun.* 28:785-791.

Nisonoff, A. and E. Lamoyi. 1981. Implications of the presence of an internal image of the antigen in anti-idiotypic antibodies: possible application to vaccine production. *Clin. Immunol. Immunopathol.* 21:397-406.

Pepys M. B. 1972. Role of complement in induction of the allergic response. Nature [New Biol] 273:157.

Pepys, M. B. 1974. Role of complement in induction of antibody production in vivo. J. Exp. Med.140:126.

Rice, P.A. and D.L. Kasper. 1977. Characterization of gonococcal antigens responsible for induction of bactericidal antibody in disseminated infection. *J. Clin. Invest.* 60:1149-1158.

Rice, P.A. and D.L. Kasper. 1982. Characterization of serum resistance of *Neisseria gonorrhoeae* that disseminate. *J. Clin. Invest.* 70:157-167.

Rice, P.A., H.E. Vayo, M.R. Tam and M.S. Blake. 1986. Immunoglobulin G antibodies directed against protein III block killing of serum resistant *Neisseria gonorrhoeae* by immune serum. *J. Exp. Med.* 164:1735-1748.

Rice, P.A. 1989. Molecular basis for serum resistance in *Neisseria gonorrhoeae*. *Clin. Micro. Rev.* 2S:S112-S117.

Roberts, R.B. 1967. The interaction in vitro between Group B meningococci and rabbit polymorphonuclear leukocytes. *J. Exp. Med.* 126:795-817.

Romero, P.J., J.P. Tam, D. Schlesinger, P. Clavijo, P.J. Barr, R.S. Nussenzweig, V. Nussenzweig and F. Zavala. 1988. Multiple T helper cell epitopes of the circumsporozoite protein of *Plasmodium berghei*. Eur. J. Immunol. 18: 1951-1957.

Ross, S.C. and P. Densen. 1985. Opsonophagocytosis of *Neisseria gonorrhoeae*: interaction of local and disseminated isolates with complement and neutrophils. *J. Infect. Dis.* 151:33-41.

Schaaper, W.M., Lu, Y.A., Tam, J.P. and R.H. Meloen. 1990. p. 765. In: Peptides: Chemistry, Structure and Biology. Rivier, I.E. and G.R. Marshall (eds.). ESCOM Science Publishers, Leiden.

Schoolnik, G.K. and Mietzner, T.A. 1992. Vaccines against gonococcal infections. In: G.C. Woodrow and M.M. Levine (ed.), *New Generation Vaccines*, Marcel Dekker, Inc. New York, 565-597.

Schoolnik, G.K. and Z.A. McGee. 1985. Gonococcal vaccine development strategies: summary of the recommendations of a National Institutes of Health vaccine panel. In: G.K. Schoolnik, G.F. Brooks, S. Falkow, C.E. Frasch, J.S. Knapp, J.A. McCutchan and S.A. Morse (ed.), *The pathogenic neisseria*. ASM, Washington D.C., 329-331.

Schreiber, J.R., M. Patarawan, M. Tosi, J. Lennon and G.B. Pier. 1990. Anti-idiotype-induced lipo-oligosaccharide specific antibody response to *Pseudomanas aeroginosa*. J. Immun. 144:1023-1029.

Schreiber, J.R., G.B. Pier, M. Grout, K. Nixon and M. Patawaran. 1991. Induction of opsonic antibodies to *Pseudomonas aeroginosa* mucoid exopolysaccharide by an anti-idiotypic monoclonal antibody. *J. Infect. Dis.* 164:507-514.

Shinnick, T.M., J.G. Sutcliff, N. Green and R. Lerner. 1983. Synthetic peptide immunogens as vaccines. Annu. Rev. Microbiol. 37: 425-446.

Smith, G.P. and J.K. Scott. 1993. Libraries of peptides and proteins displayed on filamentous phage. Methods Enzymol. 217: 228-257.

Stein, K.E. and T. Soderstrom. 1984. Neonatal administration of idiotype or anti-idiotype primes for protection against *Escherichia coli* K13 infection in mice. *J. Exp. Med.* 160:1001-1011.

Swanson, J. 1982. Colony opacity and protein II compositions of gonococci. *Infect.Immun.* 37:359-368.

Tramont, E.C., J.C. Sadoff and M.S. Artenstein. 1974. Cross-reactivity of *Neisseria gonorrhoeae and Neisseria menigitidis* and the nature of antigens involved in the bactericidal reaction. *J. Infect. Dis.* 130:240-247.

Tramont, E.C. and J. Ciak. 1978. Antigonococcal antibodies in genital secretions. In: G.F. Brooks, E.C. Gotschlich, W.D.Sawyer and F.E. Young (ed.), *Immunobiology of Neisseria gonorrhoeae* (ASM, Washington DC), 274-278.

Tramont, E.C., J.W. Boslego, R. Chung, D. McChesney, J. Ciak, J. Sadoff, M. Piziak, C.C. Brinton, S. Wood and J. Bryan. 1985. Parenteral gonococcal pilus vaccine. In: G.K. Schoolnik, G.F. Brooks, S. Falkow, C.E. Frasch, J.S. Knapp, J.A. McCutchan and S.A. Morse. (eds.), *The pathogenic Neisseria*. (ASM, Washington DC), 316-322.

Tramont, E.C. 1989. Gonococcal vaccines. *Clin. Micro. Rev.* 2S:S74-S77.

Ward, E.S., D. Güssow, A.D. Griffiths, P.T. Jones and G. Winter. 1989. Binding activities of a repertoire of a single immunoglobulin variable domains secreted from *Escherichia coli*. Nature 341: 544-546.

Ward, M.E., P.R. Lambden, J.E. Heckels and P.J. Ward. 1978. The surface properties of *Neisseria gonorrhoeae*: determinants of susceptibility to antibody complement killing. *J. Gen. Microl.* 108:205-212.

Ward, M.M., R.E. Ward, J.H. Huang and H. Kohler. 1987. Idiotope vaccine against *Streptococcus pneumonia*: A precursor study. *J. Immunol.* 139:2775-2780.

Washington, A.E. 1982. Update on treatment recommendations for gonococcal infections. *Rev. Infect. Dis.* 4S:S758-S771.

Westerink, M.A., P.C. Giardina, M.A. Apicella and T. Kieber-Emmons. 1995. Peptide mimicry of the meningococcal group C capsular polysaccharide. Proc. Natl. Acad. Sci. USA. 92: 4021-4025.

Zavala, F., J.P. Tam, M.R. Hollingdale, A.H. Cochrane, I. Quakyi, R.S. Nussenzweig and V. Nussenzweig. 1985. Rationale for development of a synthetic vaccine against Plasmodium falciparum malaria. Science 228: 1436-1440.

* cited by examiner

Figure 1
A. Probe with mAb 2C7
B. Probe with anti-thioredoxin antibody

Figure 2

| | | |
|---|---|---|
| PEP1 | IPVLDENGLFAP | [SEQ ID NO 1] |
| PEP2 | WGLDYERGNYEE | [SEQ ID NO 2] |
| PEP3 | DALAVDQMGRFG | [SEQ ID NO 3] |
| PEP4 | VLVGEKGLFEGG | [SEQ ID NO 4] |
| PEP5 | EALVLDTNGLMS | [SEQ ID NO 5] |
| PEP6 | ADRTQGLGWGAS | [SEQ ID NO 6] |
| PEP7 | EEVGSILYGLGG | [SEQ ID NO 7] |
| CONSENSUS | DE-GLF | [SEQ ID NO 8] |

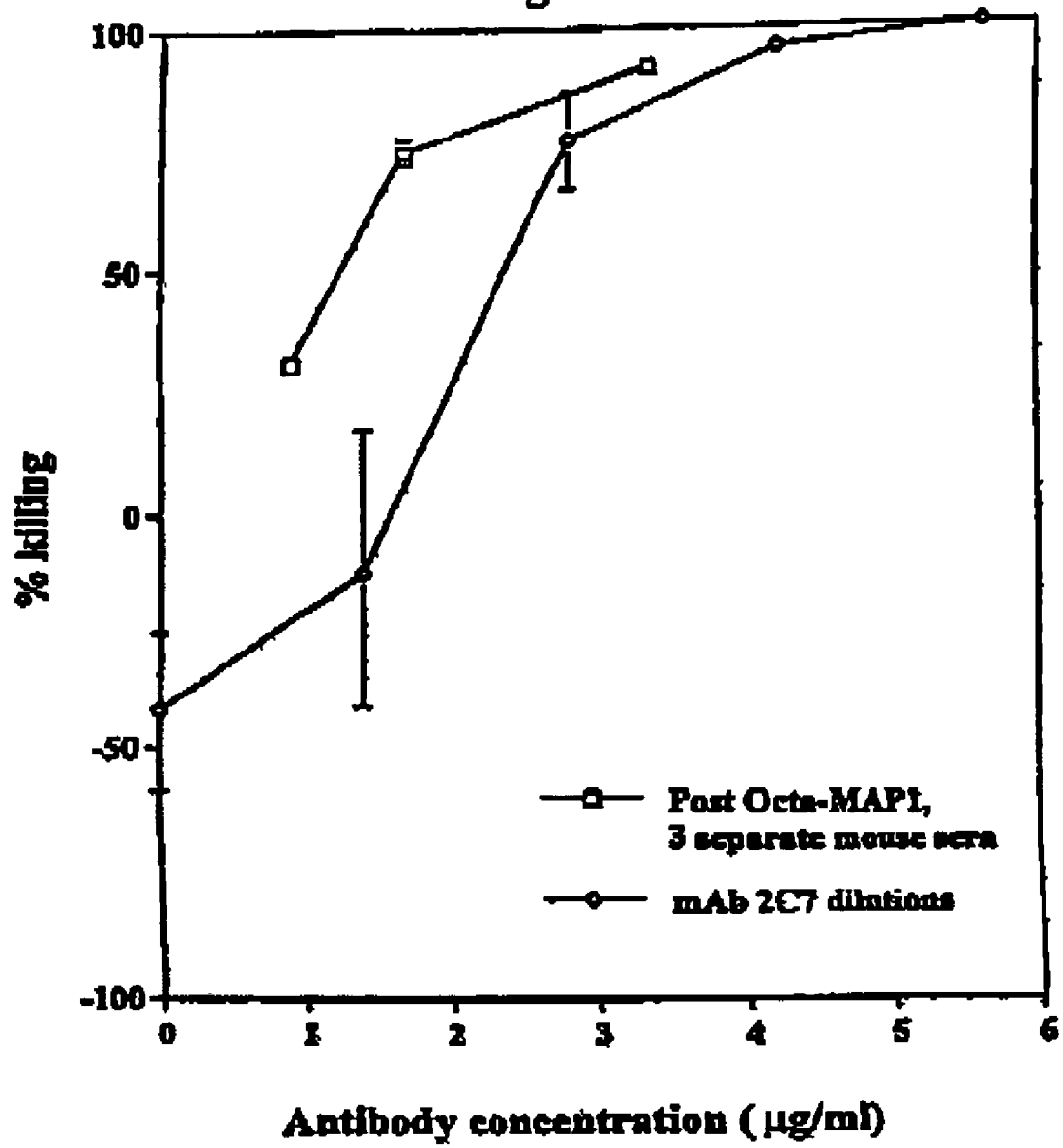

PEPTIDE MIMICS OF CONSERVED GONOCOCCAL EPITOPES AND METHODS AND COMPOSITIONS USING THEM

This application claims the benefit of U.S. provisional application 60/162,491 filed Oct. 29, 1999, which is hereby incorporated by reference herein in its entirety.

TECHNICAL FIELD OF THE INVENTION

The present invention relates to peptide mimics of conserved epitopes of *Neisseria gonorrhoeae*, which epitopes are not found on human blood group antigens. This invention also relates to methods and compositions using such peptide mimics for the prophylaxis of gonorrheal infections.

BACKGROUND OF THE INVENTION

The sexually transmitted disease, gonorrhea, poses a worldwide risk as one of the most commonly reported communicable diseases. Gonorrhea is caused by the bacterium *Neisseria gonorrhoeae*, a gram negative diplococcus. Although the pathogen primarily infects mucous membranes, it is capable of invading tissues and evading host defenses. *N. gonorrhoeae* is the causative agent of a spectrum of sequelae. These range from asymptomatic mucosal infection to significant disease syndromes in both men and women. The more serious of such syndromes include, for example, disseminated gonococcal infection ("DGI") in men and women, as well as salpingitis or pelvic inflammatory disease ("PID") in women. Either salpingitis or PID may themselves lead to long-term sequelae, including ectopic pregnancy and infertility. Other important sequelae, sometimes requiring surgical intervention, include recurrent infection, chronic pelvic pain, dyspareunia, pelvic adhesions and other inflammatory residua.

It has been estimated that in the United States, the direct and indirect costs of treating PID and associated ectopic pregnancy and infertility totaled 2.6 billion dollars in 1984 (53). The total direct costs were estimated to be 2.18 billion dollars in 1990, with indirect costs of 1.54 billion dollars. Assuming constant inflation and incidence rates of PID, the total cost of this disease is projected to reach 8 billion dollars in the year 2000 (9).

Despite public health efforts to control gonococcal infections and the availability of effective antibiotic therapies in the United States, there are approximately 315,000 cases of gonorrhea reported annually to the Centers for Disease Control ("CDC") (12). A substantial proportion of all cases of gonorrhea occur in asymptomatically infected individuals who are the source of most new cases within a community (6). The increasing prevalence of antibiotic-resistant strains has complicated treatment of the infection (10, 11, 52).

*N. gonorrhoeae* has multiple virulence factors. The surface components of this pathogen play an important role in attaching to and invading host cells, while providing potential targets for the host immune response. Gonococcal infections elicit local and systemic humoral and cellular immune responses to several components which are exhibited as surface exposed antigens of the bacterium, particularly pili, porin ("Por") or protein I ("PI"), opacity associated proteins ("Opas") or protein IIs, Rmp or protein III, and lipooligosaccharides ("LOSs") (7). Pili, Opa, Por and LOS are all implicated in attachment to and invasion of the host and all display considerable variation on their surface exposed regions (26, 45, 46). The intra- and inter-strain variations of gonococcal surface components have led to hypotheses regarding tissue specificity at different sites and the organism's potential for reinfection and continued virulence.

In both symptomatic and asymptomatic patients, gonococcal infections have been shown to stimulate increased levels of anti-gonococcal serum immunoglobulins. The peripheral humoral response is predominately IgG (mostly subclass IgG3), with lesser amounts of IgM and IgA (13). Quantitatively, the antibody response is primarily directed against the pili, Opa proteins and LOS. Local antibodies are present in genital secretions, but in reduced amounts (48), and may be directed against different antigenic targets than those in serum (27). The predominant class of antibodies present in secretions is also IgG (mostly IgG3) and not secretory IgA ("sIgA") (7). Antibodies against LOS are present as well, but in lesser amounts than those against pili, Por and Opa. Although patients infected with *N. gonorrhoeae* may show an antibody response to many gonococcal antigens, *N. gonorrhoeae* isolated from patients with disseminated infection (DGI) are resistant to the bactericidal action of normal human serum ("NHS") and of most convalescent sera (38). This serum-resistant phenotype, termed stable serum resistance ("SR"), may enable the organism to evade local defenses, penetrate mucosal barriers and disseminate via the bloodstream.

Upon subculture, many strains of gonococci become phenotypically sensitive to killing by NHS or serum sensitive (38). These organisms are termed serum sensitive ("SS") or unstably serum-resistant. Such organisms are frequently isolated from women with severe manifestations of local inflammation or clinically evident PID. Acute salpingitis, the pathologic counterpart of PID (caused by SS gonococci), rarely progresses to bacteremic illness or DGI. This suggests that the intense local inflammatory response, generated by SS gonococci, may serve to contain the infection and prevent bacteremia, although at the cost of damaging the local tissues. SS gonococci generate significantly greater amounts of the complement derived chemotactic peptide, C5a, than do SR gonococci (16). This may be responsible for the polymorphonuclear leukocyte ("PMN") mediated inflammatory response that is produced by SS gonococci.

The development of antibiotic-resistant strains of *N. gonorrhoeae*, has rendered control of this infection increasingly difficult. The potential to undertreat gonococcal infection has accelerated the need for an anti-gonococcal vaccine. The prevention of gonococcal infection, particularly the severe complications of PID, has been the goal of many investigators. Ongoing attempts to develop an effective anti-gonococcal vaccine, however, have been plagued with several difficulties.

Attempts to use individual surface components of the pathogen as targets for conventional vaccines have been unsuccessful because of their antigenic variability. Pilus vaccines have been protective only against infection with the homologous strain (used to make the pilus vaccine) and Por vaccination has been unsuccessful even in human experimental challenge. In addition, *N. gonorrhoeae* express marked phenotypic heterogeneity, typically shifting from one antigenic form to another at a frequency of >1 in $10^3$ organisms (49, 50) making the surface of this organism a moving target for most vaccine strategies. Although the vaccine candidates have provoked antibody responses, the antibodies and immune responses produced have not been broadly protective.

LOS is an important virulence determinant of *N. gonorrhoeae*. Considerable evidence supports the role of LOS as a major target of bactericidal antibody directed to the surface of *N. gonorrhoeae* (2, 16, 18, 37, 47). Antibodies to LOS have several important functions: bactericidal activity, complement activation through the classical or alternative complement pathways (2), and opsonic activity (16). Additionally, LOS has been shown to be the most effective gonococcal antigen to induce a functional antibody response to homologous and heterologous gonococci (51).

The monoclonal antibody ("mAb") 2C7 (30), detects a LOS derived oligosaccharide ("OS") epitope that appears to be widely conserved and expressed amongst clinical isolates of gonococci. Typically, saccharides are T-cell independent antigens. When administered alone as immunogens, they generally elicit only a primary antibody response. In addition, oligosaccharides are small (<10 saccharide units) (19), and would likely require additional biochemical derivatization to render them immunogenic. The use of such oligosaccharides as vaccine candidates, therefore, is limited in several respects.

Internal image determinants have been proposed for use in vaccines (36). By means of mAb technology, a protective antibody (Ab1) to an epitope of interest on the pathogen can be produced. The particular antibody (Ab1) can be purified and subsequently used as an immunogen to elicit an anti-idiotypic antibody (Ab2) which may be an internal image of the original epitope on the pathogen.

As predicted by the Jerne "network" theory (23), immunization with an anti-idiotypic antibody (Ab2) that is directed against antigen combining sites of primary antibody (Ab1), may elicit a humoral immune response specific for the nominal antigen. The resulting anti-anti-idiotypic antibody (or Ab3) should react with the original primary antigen. If the primary antigen is an oligosaccharide (and therefore expected to give a T-cell independent immune response), then immunization with Ab2 (the protein equivalent) may elicit a T-cell dependent response.

It has been demonstrated that an anti-idiotope of mAb 2C7 elicits anti-LOS antibodies in mice and rabbits that together with complement are bactericidal for gonococci, and that serum from animals immunized with this anti-idiotypic antibody also supports opsonophagocytosis by human PMNs (20).

It has also been shown that synthetic peptides which mimic a nominal antigen through binding to a specific antibody directed to the nominal antigen can also elicit an immune response against the nominal antigen (29, 24, 54).

The need exists for an agent useful for the prevention of gonorrhea targeted to the prevention of gonococcal salpingitis, an infection that may be associated with debilitating and chronic pelvic pain, infertility and ectopic pregnancy (42). Another important objective is to prevent transmission of the organism from an infected but asymptomatic host to an otherwise immune sexual consort. This is important because a substantial fraction of all cases of gonorrhea in both men and women are asymptomatic, and asymptomatically infected, sexually active persons are probably the major source of most new infections. Accordingly, a gonococcal vaccine that only attenuates the severity of symptomatic gonorrhea could result in a higher ratio of asymptomatic/symptomatic cases and as a result, such a vaccine might promote the spread of gonorrhea, unless it also prevents transmission (41).

SUMMARY OF THE INVENTION

The present invention generally solves the problems referred to above by providing peptide mimics of widely conserved oligosaccharide epitopes of *N. gonorrhoeae* which are not present in human blood group antigens. Also provided are methods for producing the peptide mimics according to this invention.

The peptide mimics according to this invention are useful in methods and compositions for the prophylaxis of *N. gonorrhoeae* infections.

BRIEF DESCRIPTION OF THE DRAWINGS

FIG. 1 shows a Western blot analysis of the binding of mAb 2C7 to *E. coli* clones. The seven unique *E. coli* clones (PEP1–PEP7) [SEQ ID NOS:1–7] were grown in IMC media containing 100 μg/ml ampicillin, and then induced to express fusion proteins. Bacterial lysates from each of the clones were prepared and loaded onto 14% SDS-PAGE gels. After electrophoresis, the proteins were transferred to Immobilon PVDF transfer membranes using a Biorad electrophoretic transfer apparatus (Biorad, Hercules Calif.). The membranes were probed with mAb 2C7 (A) or anti-thioredoxin antibody (B). A negative clone that did not bind mAb 2C7 was used as a control [SEQ ID NO:9].

FIG. 2 shows the peptide mimic sequences derived from the seven *E. coli* clones that bind to mAb 2C7.

FIG. 12 controls included the Complement source without antibody (137.9%±1.0% survival (no killing) for strain 15253, and 132.5%±14.3% survival (no killing) for the lgtG mutant of 15253).

FIG. 13 shows a plot of IgG anti-LOS antibody concentration versus killing of N. gonorrhoeae strain 15253. IgG anti-LOS antibody levels from each of three mice immunized with Octa-MAP1 are plotted versus percent bacterial killing. Mouse sera containing 1.38, 2.50 and 5.05 μg/ml of anti-LOS antibodies showed 31, 74 and 92% killing respectively of strain 15253. Killing by mAb 2C7 is shown at 5 separate LOS antibody concentrations as a positive control.

DETAILED DESCRIPTION OF THE INVENTION

Definitions

Figure 3:
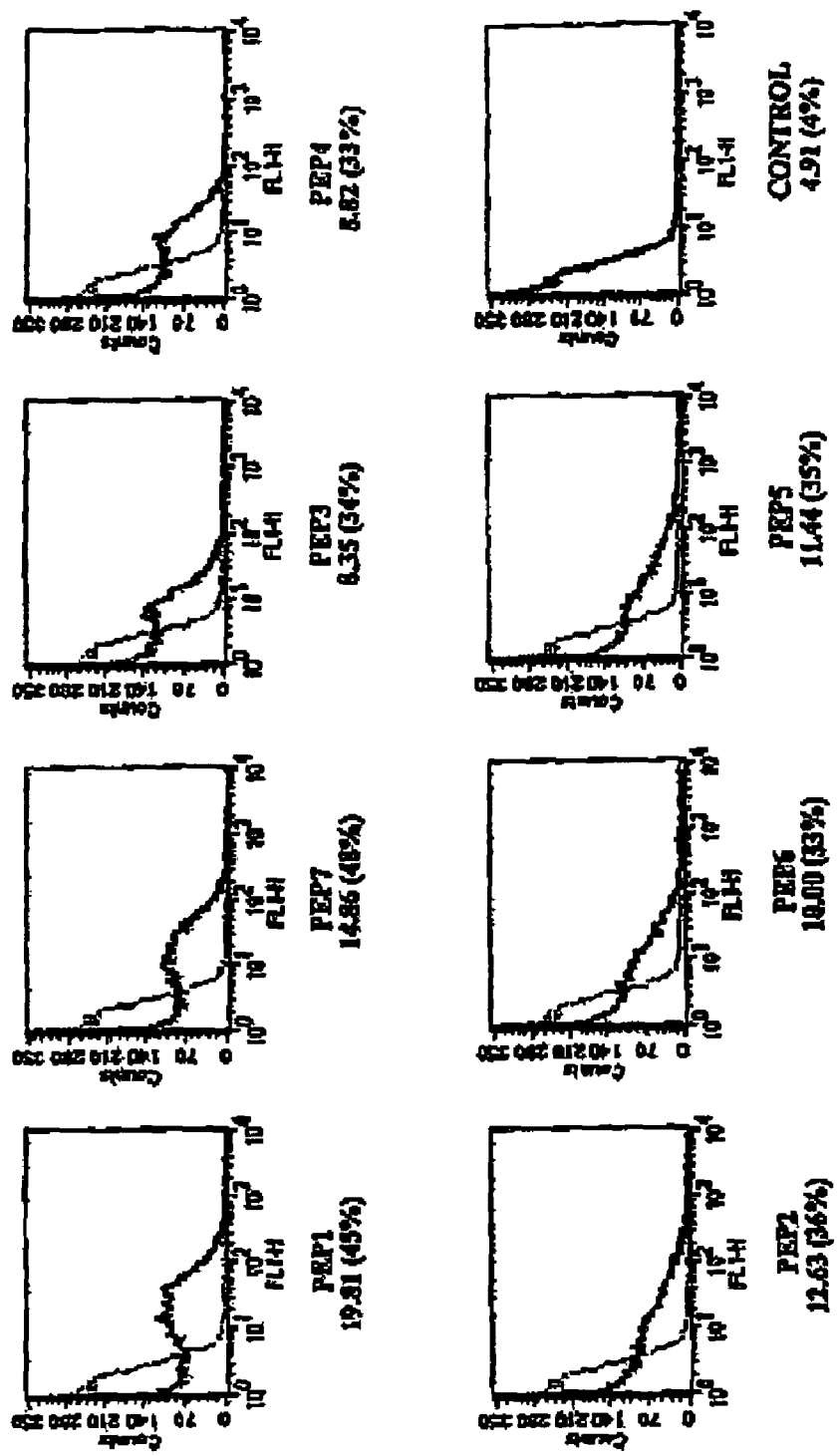
FIG. 3 shows FACS analysis of mAb 2C7 binding to *E. coli* clones expressing peptide mimic fusions. *E. coli* clones were grown in IMC media containing 100 μg/ml ampicillin, and then induced to express fusion proteins. The bacterial cells were fixed with 1% paraformaldehyde before staining with mAb 2C7, followed by FITC-conjugated anti-mouse IgG. A negative clone that did not bind mAb 2C7 was used as a control [SEQ ID NO:9]. The number below the *E. coli* clones represents the median fluorescent intensity in the populations that bind to mAb 2C7 compared to the control; the number in parenthesis shows the percentage of the cells in the population (total population=100%).

As used herein, an "antibody" is an intact immunoglobulin molecule comprising two each of immunoglobulin light and heavy chains. Accordingly, antibodies include intact immunoglobulins of types IgA, IgG, IgE, IgD, IgM (as well as subtypes thereof), wherein the light chains of the immunoglobulin may be of types kappa or lambda.

As used herein, "monoclonal antibodies" are monospecific antibodies produced initially by a single clone of antibody forming cells.

As used herein, "immunoprophylactically effective" means the ability to induce in a normal individual an immune response sufficient to protect said patient for some period of time against N. gonorrhoeae infection.

As used herein, "peptide" means a linear or cyclic chain of amino acids, usually at least 4 and less than 50 amino acids in length.

As used herein, "peptide mimic" means a peptide which exhibits an immunological antibody binding profile similar to that of a known epitope.

PEPTIDE MIMICS AND THEIR USE IN COMPOSITIONS AND METHODS ACCORDING TO THIS INVENTION

The present invention is directed to peptide mimics that immunospecifically react with an antibody directed to a conserved oligosaccharide epitope of N. gonorrhoeae, which oligosaccharide epitope is not present in human blood group antigens. Such peptide mimics can be used in a manner similar to the anti-idiotypic antibodies described, for example in U.S. Pat. Nos. 5,476,784 and 6,099,839 (both incorporated herein by reference), as a surrogate antigen to elicit a T cell-dependent immune response against an oligosaccharide epitope of N. gonorrhoeae.

The peptide mimic may be administered to uninfected individuals to induce a specific immune response directed against gonococcal organisms or cells bearing said oligosaccharide antigen. Such an immune response can be immunoprophylactic in character, in that it would prevent an infection should the recipient be exposed to the gonococcal organism or cells bearing said oligosaccharide antigen.

A random peptide library may be screened based on antibody binding specificity in order to identify candidate peptide mimics. The technology for such screening is known to those of skill in the art. In one approach, a random peptide library expressed on E. coli flagella may be used to identify peptides that bind to a conserved oligosaccharide epitope of N. gonorrhoeae, which oligosaccharide epitope is not present in human blood group antigens. For example, binding to mAb 2C7 may be assayed to identify candidate peptide mimics. Binding may be characterized by western blotting, flow cytometric analysis or competition for binding of mAb 2C7 to LOS by solid-phase ELISA.

Antibody modeling may also be used to define an immunogenic site in the complementarity determining regions (CDRs) of an anti-idiotope corresponding to the epitope of interest. Such analysis may yield information about the three-dimensional conformation of the immunogenic site that is useful in the design of a peptide mimic of the immunogenic site.

Once a specific peptide mimic is identified and sequenced, it may be produced synthetically by methods known in the art.

Peptide mimics may also be modified to elicit a greater immune response through the use of haptens, the use of adjuvants, linking the peptide mimic to a carrier protein, using a multiple antigen peptide, coupling the peptide mimic to a complement protein or through other methods known in the art.

The preferred pharmaceutical compositions of this invention are similar to those used for immunization of humans with other peptides. Typically, the peptide mimics of the present invention will be suspended in a sterile saline solution for therapeutic uses. The pharmaceutical compositions may alternatively be formulated to control release of the active ingredients or to prolong their presence in a patient's system. Numerous suitable drug delivery systems are known and include, e.g., implantable drug release systems, hydrogels, hydroxymethylcellulose, microcapsules, liposomes, microemulsions, microspheres, and the like.

The pharmaceutical compositions of this invention may be administered by any suitable means such as orally, intranasally, subcutaneously, intramuscularly, intravenously, intra-arterially, or parenterally. Ordinarily, intravenous (i.v.) or parenteral administration will be preferred.

It will be apparent to those of ordinary skill in the art that the immunoprophylactically effective amount of peptide mimics of this invention will depend, inter alia, upon the administration schedule, the unit dose of peptide mimic administered, whether the peptide mimic is administered in combination with other therapeutic agents, the immune status and health of the patient, the therapeutic activity of the peptide mimic administered and the judgment of the treating physician.

In order that this invention may be better understood, the following examples are set forth. These examples are for purposes of illustration only, and are not to be construed as limiting the scope of the invention in any manner.

EXAMPLES

I. Identification of Clones that Encode Peptides that Specifically Bind to mAb 2C7

A. Random Peptide Display

A FliTrx™ random peptide library (Invitrogen, Carlsbad Calif.) was used to express peptides (12-mers) of random sequence on the surface of *E. coli*. The DNA encoding this library of peptides is inserted within the gene encoding the active loop of thioredoxin which is itself inserted into the nonessential region of the flagellin gene. Expression of the peptide fusion is controlled by the bacteriophage lambda major leftward promoter ($P_L$) in the vector pFliTrx™. In this system, $P_L$ is induced by the addition of tryptophan. When induced, the fusion protein is exported and assembled into flagella on the bacterial cell surface, allowing for the display of the peptide.

B. Screening of Peptides that Bind to mAb 2C7

The FliTrx™ peptide library ($1.77 \times 10^8$ primary clones) was grown overnight in IMC medium (0.2% w/v casamino acid, 0.5% w/v glucose, 42 mM $Na_2HPO_4$, 22 mM $KH_2PO_4$, 8.5 mM NaCl, 18.7 mM $NH_4Cl$ and 1 mM $MgCl_2$) containing 100 µg/ml ampicillin, at 25° C. The expression of fusion peptides was induced by adding L-tryptophan to a final concentration of 100 µg/ml, and the culture was grown at 25° C. for 6 h. The induced peptide fusion library was then incubated with a 2C7 mAb-coated plate (20 µg/ml). After 1 h incubation, the plate was washed 5 times with IMC medium containing 100 µg/ml ampicillin and 1% α-methyl mannoside. Bound *E. coli* were eluted by mechanical shearing or by competition with purified LOS prepared from gonococcal strain 15253 (the mAb 2C7 epitope is known to be expressed in strain 15253), and then grown overnight at 25° C. After the fifth round of panning, bound *E. coli* were eluted and plated on RMG agar (2% w/v casamino acid, 0.5% w/v glucose, 42 mM $Na_2HPO_4$, 22 mM $KH_2PO_4$, 8.5 mM NaCl, 18.7 mM $NH_4Cl$, 1 mM $MgCl_2$, and 1.5% agar) containing 100 µg/ml ampicillin at 25° C. Individual bacterial colonies were chosen to assay binding to mAb 2C7 by western blot (a hybridoma cell line secreting mAb 2C7 is deposited with the American Type Culture Collection ["ATCC"] and is assigned ATCC accession number HB-11859).

The library was subjected to 5 rounds of positive selection with mAb 2C7 coated on a 60 mm tissue culture plate or subjected to negative selection for 1 h with irrelevant IgG3 (Sigma, St. Louis, Mo.) first, before proceeding to 5 rounds of positive selection with mAb 2C7.

One hundred-seven colonies were randomly chosen and screened by western blot for the ability to bind mAb 2C7. Fourteen clones were identified that bound to mAb 2C7. Plasmid DNA was then prepared from the positive clones and sequenced using primers that bind to regions that are located at the 5' and 3' flanks of the inserted peptide's nucleotide sequence. Seven unique clones were identified, as shown in FIGS. 1 and 2 [SEQ ID NOS:1–7].

C. Flow Cytometric Analyses

Positive *E. coli* clones were grown overnight in IMC media containing 100 µg/ml ampicillin, at 25° C. and then induced to express the peptide fusions for 6 h. *E. coli* cells were fixed with 0.5% paraformaldehyde on ice for 10 min. Aliquots of 200-µl of fixed organisms were spun at 2000×g for 10 min. Supernatants were discarded, and pellets were resuspended in blocking buffer (IMC media containing 100 µg/ml ampicillin, 1% nonfat dry milk, 150 mM NaCl and 1% α-methyl mannoside) containing mAb 2C7. Suspensions were incubated at 37° C. for 30 min. before spinning at 2000×g for 10 min. Pellets were washed with 100 µl of washing buffer (IMC media containing 100 µg/ml ampicillin and 1% α-methyl mannoside) and then resuspended in 100 µl of blocking buffer containing FITC-conjugated anti-mouse IgG (Sigma, St. Louis, Mo.). The mixtures were incubated at 37° C. for 30 min before spinning at 2000×g for 10 min. Supernatants were removed, and pellets were washed in 100 µl of washing buffer before resuspension in 1 ml of PBS. The suspensions were analyzed on a FACS using CELLQUEST™ Flow Cytometry Software (Becton Dickinson, Franklin Lakes N.J.). A negative clone that did not bind mAb 2C7 was used as a control.

The binding of *E. coli* cells to mAb 2C7 was observed to increase from *E. coli* clone PEP3, PEP4, PEP6, PEP5, PEP2, PEP7 to PEP 1 (according to median fluorescent intensity, "MFI") [SEQ ID NOS:3, 4, 6, 5, 2, 7 and 1]. *E. coli* clone PEP1 showed the maximum binding to mAb 2C7 (MFI=19.81, compared to control MFI=4.91), as shown in FIG. 3 [SEQ ID NO:1].

D. Inhibition ELISA

Positive *E. coli* clones were grown overnight in IMC media containing 100 µg/ml ampicillin at 25° C., and then induced to express the peptide fusions for 6 h. Cultures were normalized to the same OD reading ($OD_{600}$ nm≈0.7), and 1% nonfat dry milk, 150 mM NaCl and 1% α-methyl mannoside were added to block nonspecific binding. 50 µl-aliquots of each culture were incubated with 50 µl of mAb 2C7 (final concentration 20 ng/ml) at 37° C. for 30 min, then 100 µl of the mixtures were loaded into microtiter plate wells coated with purified LOS prepared from strain 15253 (80 µg/ml). The wells were incubated at 37° C. for 1 h, then washed. After the wells were washed, bound mAb 2C7 was detected with anti-mouse IgG conjugated to alkaline phosphatase. A negative clone that did not bind mAb 2C7 was used as a control.

Figure 4:
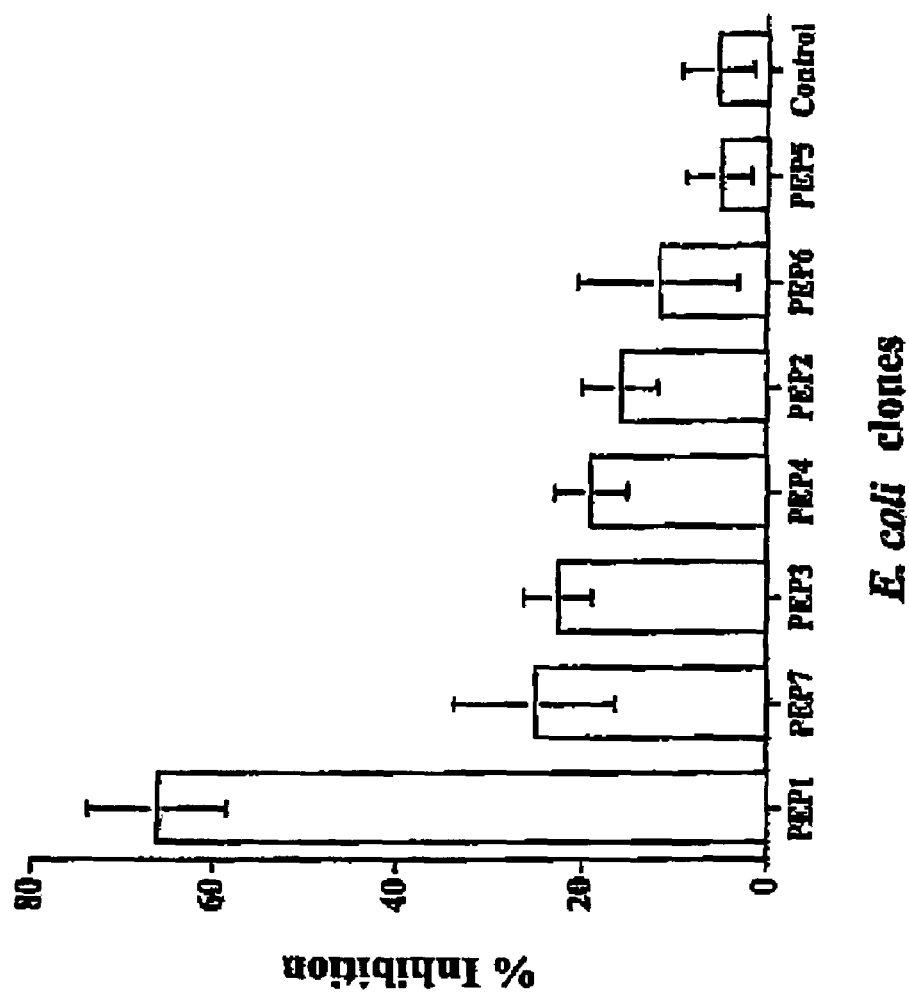
FIG. 4 shows inhibition of mAb 2C7 binding to LOS by *E. coli* clones expressing peptide fusions. *E. coli* clones were grown in IMC media containing 100 μg/ml ampicillin, and then induced to express fusion proteins. *E. coli* cells were incubated with mAb 2C7 for 30 min. before loading onto LOS coated plates. A negative clone that did not bind mAb 2C7 was used as a control [SEQ ID NO:9]. The data represent means from at least 2 experiments (duplicate wells). PEP1 clones showed the maximum inhibition of mAb 2C7 binding to LOS (66%) [SEQ ID NO:1]. PEP7, PEP3, PEP4, PEP2, PEP6, and PEP5 showed respective decreases in inhibition of binding [SEQ ID NOS:7, 3, 4, 2, 6 and 5, respectively].

PEP1 clones showed the maximum inhibition of mAb 2C7 binding to LOS (66%) [SEQ ID NO:1]. PEP7, PEP3, PEP4, PEP2, PEP6, and PEP5 showed respective decreases in inhibition of binding, as depicted in FIG. 4 [SEQ ID NOS:7, 3, 4, 2, 6 and 5]. The inhibition ELISA results correlated with the flow cytometric analysis results in that PEP1 also showed the maximum binding to mAb 2C7. The binding of *E. coli* cells to mAb 2C7 correlated approximately with decreases in inhibition of mAb 2C7 binding to LOS by *E. coli* clones.

II. Synthetic Peptide Mimic Binding to mAb 2C7

A synthetic peptide (PEP1; IPVLDENGLFAP [SEQ ID NO:1]) whose sequence corresponds to the consensus sequence "DE_GLF" and includes two cysteine flanking regions (CGP- and -GPC residues at the [[N]]- and C-terminus, respectively) was synthesized (Boston Biomolecules, Mass.) to assess specific binding to 2C7 mAb by inhibition ELISA and to determine whether peptide mimics characterized as thioredoxin-fusion proteins would retain the antigenicity independent of the fusion context [SEQ ID NO:10].

The cysteine flanking regions were added to assess whether antibody binding is affected by cyclization of the peptide mimic. In these peptides mimics, the cysteine residues allow for the formation of a disulfide bond between them, resulting in a cyclic peptide mimic. Such conformationally constrained peptides may more closely resemble the epitope that they mimic, and therefore may be more immunogenic.

Peptides were diluted in blocking buffer (1% ovalbumin, 0.05% TWEEN-20™ (polysorbate 20), 0.5 M NaCl in PBS) to produce mixtures of varying concentrations (0.1, 0.5 and 1 mg/ml). 50 µl-aliquots from each of the concentrations were incubated with 50 µl of mAb 2C7 (stock concentration 2 µg/ml diluted in blocking buffer) at 37° C. for 1 h, then 100 µl of the mixtures were loaded into microtiter plate wells coated with purified LOS prepared from strain 15253 (80 µg/ml). The wells were incubated at 37° C. for 1 h, then washed. After the wells were washed, bound mAb 2C7 was detected with anti-mouse IgG conjugated to alkaline phosphatase. Purified LOS prepared from gonococcal strain 15253 was used as a positive control. A non-reactive 15-mer peptide sequence generated by the above described random peptide library system was used as a negative control peptide [SEQ ID NO:9].

Figure 5:
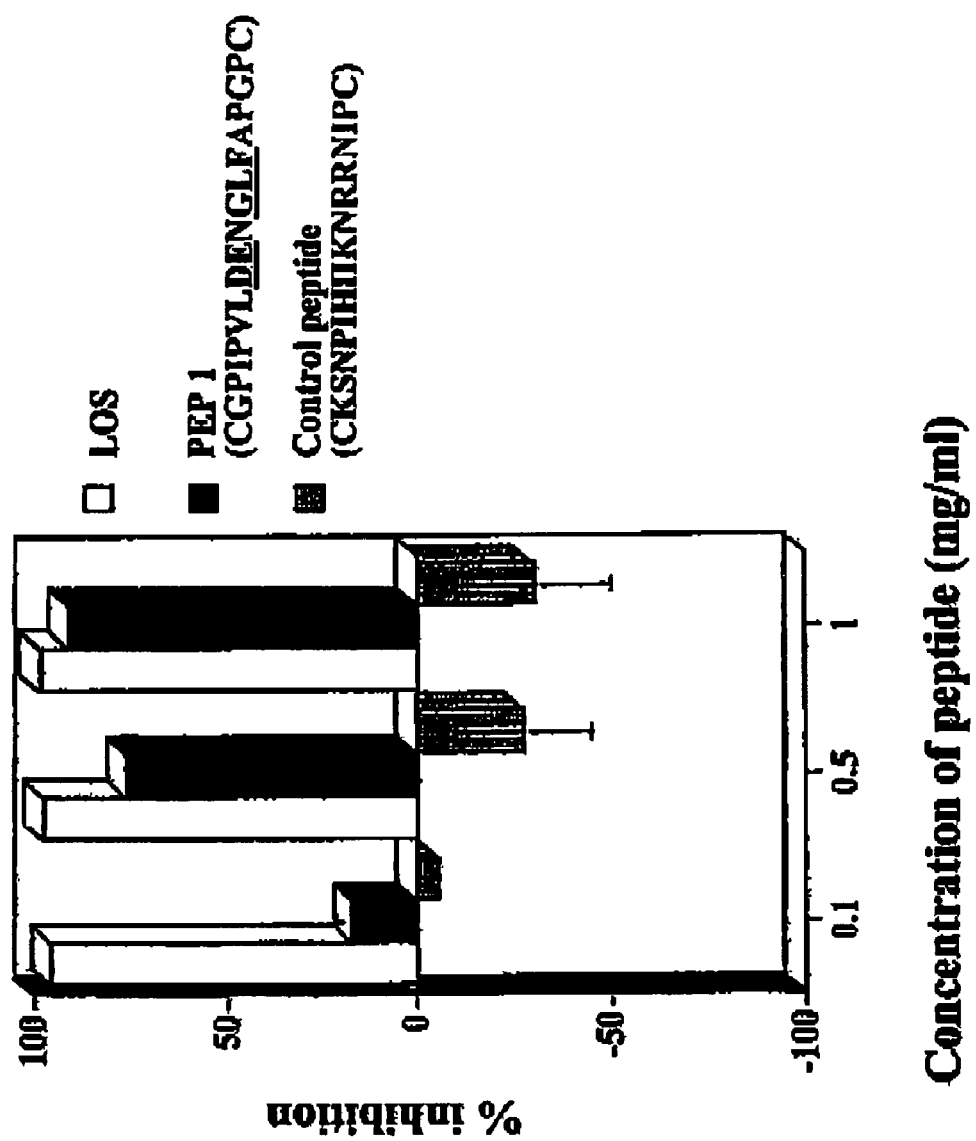
FIG. 5 shows inhibition of mAb 2C7 binding to LOS by a peptide comprising the consensus sequence (DE_GLF) [SEQ ID NO:8]. The data represent means±SE from 3 experiments (duplicate wells). Peptide PEP1 inhibited the binding of mAb 2C7 to LOS in a dose responsive manner.

PEP1 inhibited the binding of mAb 2C7 to LOS in a dose responsive manner (percentage inhibition equalled 17, 77, and 91% with concentrations of 0.1, 0.5, and 1.0 mg/ml of PEP1, respectively), as shown in FIG. 5. The control 15-mer peptide was synthesized as a cyclic peptide (*CKSNPIHI-IKNRRNIPC*) [SEQ ID NO:9]. This negative control peptide did not inhibit binding of 2C7 mAb to the purified LOS coated plate.

Cyclic peptide mimics as described immediately above may further comprise one or more "tails" for coupling to a second agent, such as an adjuvant or a carrier protein, by methods known in the art.

III. Increasing the Immunogenicity Peptide Mimics

Although small peptides may be immunogenic, several studies have reported that certain small peptides may lack immunogenicity and result in ineffective immune responses (particularly humoral responses) (3, 43). A number of strategies have been used to increase the immunogenicity of small peptides. These include linking the peptide to a carrier protein (54, 28, 54), combining the peptide with an adjuvant (21, 22), using a multiple antigen peptide (MAP) to provide a larger configurational structure that may be more immunogenic (39) and coupling the peptide to a complement protein to enhance the humoral immune response (15).

A. Multiple-Antigen Peptide Synthesis

The multiple-antigen peptide (MAP) approach is a technique which associates the peptide mimic with a dendritic matrix of lysine residues (44, 8, 43). Peptides are attached to the amino groups of the lysine scaffold to yield a macromolecule that provides a high density of desired peptide epitopes on the surface of the complex. This approach has been shown to augment the immune response to peptides (39, 40).

A multiple antigen peptide of PEP1 and a control peptide were synthesized (Boston Biomolecules, Mass.) and binding to mAb 2C7 was assayed by direct and inhibition ELISA.

Solid phase ELISA was performed to assess the binding of mAb 2C7 to multiple antigen peptides. For direct ELISA, Immulon 1 plates were coated overnight with multiple antigen peptides (1 µg/well) and reacted with varying concentration of mAb 2C7. For inhibition ELISA, plates were coated with purified LOS prepared from *N. gonorrhoeae* strain 15253 (80 µg/ml) at 37° C. for 3 h. Peptides (linear or MAPs) were diluted in blocking buffer (1% ovalbumin, 0.05% TWEEN-20™ (polysorbate 20), 0.5 M NaCl in PBS) to produce mixtures of varying concentrations. 50 µl-aliquots from each concentration were incubated with 50 µl of mAb 2C7 (stock concentration 0.4 µg/ml diluted in blocking buffer) at 37° C. for 1 h, then 100 µl of mixtures were loaded into microtiter plate wells. The wells were incubated at 37° C. for 1 h, then washed. After the wells were washed, bound mAb 2C7 was detected with anti-mouse IgG conjugated to alkaline phosphatase. Purified LOS prepared from gonococcal strain 15253 was used as a positive control in inhibition ELISA.

Figure 6:
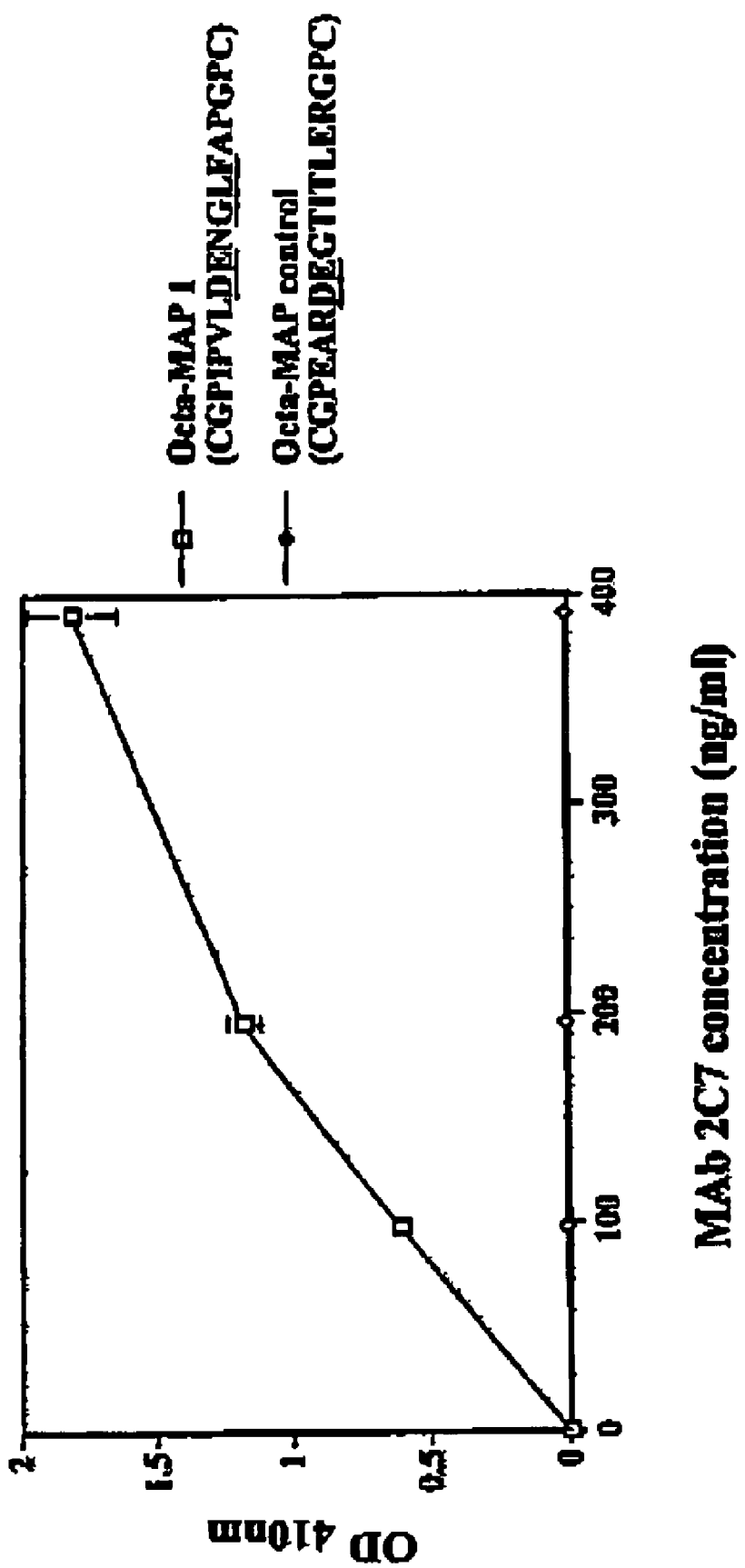
FIG. 6 shows binding of mAb 2C7 to the multiple antigen peptide ("MAP") MAP1.
Figure 7:
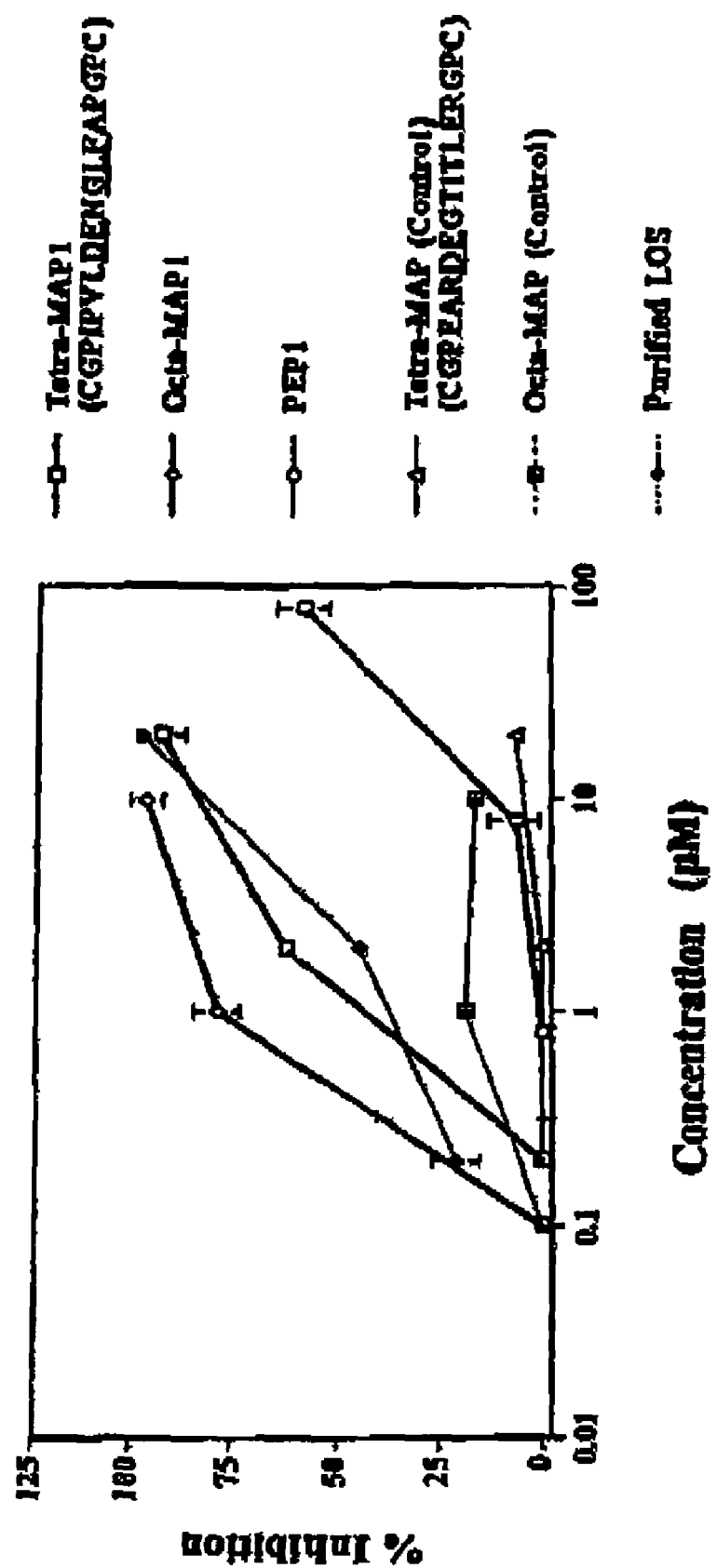
FIG. 7 shows inhibition of mAb 2C7 binding to LOS by multiple antigen peptides.

Multiple antigen peptide forms of PEP1 containing four linear PEP1 molecules ("Tetra-MAP1") or eight linear PEP1 molecules ("Octa-MAP1") showed strong binding to mAb 2C7, whereas control MAP showed no binding in direct ELISA, as depicted in FIG. 6. Both Tetra- and Octa-MAP1 inhibit mAb 2C7 binding to LOS better than linear PEP1, as depicted in FIG. 7. Half maximal inhibition ($IC_{50}$) for both tetra- and octa-MAP1 was seen at 1.26 µM and 0.23 µM respectively. $IC_{50}$ for linear PEP1 55 µM. This may be due to increased avidity of MAP1 binding to mAb 2C7. Control MAPs showed no significant inhibition.

Immunization with octa-MAP1 induces an IgG anti-LOS antibody response in mice, as shown in FIGS. 8A–8D. The response profile seen in FIG. 8(A), in which there is no significant IgG anti-LOS response until the boost at week 3, indicates that the Octa-MAP1 elicited a T-cell dependent immune response in the responding mice. These results demonstrate the promise of a peptide mimic, such as Octa-MAP1, for immunizing humans against *N. gonorrhoeae* infection.

Figure 8:
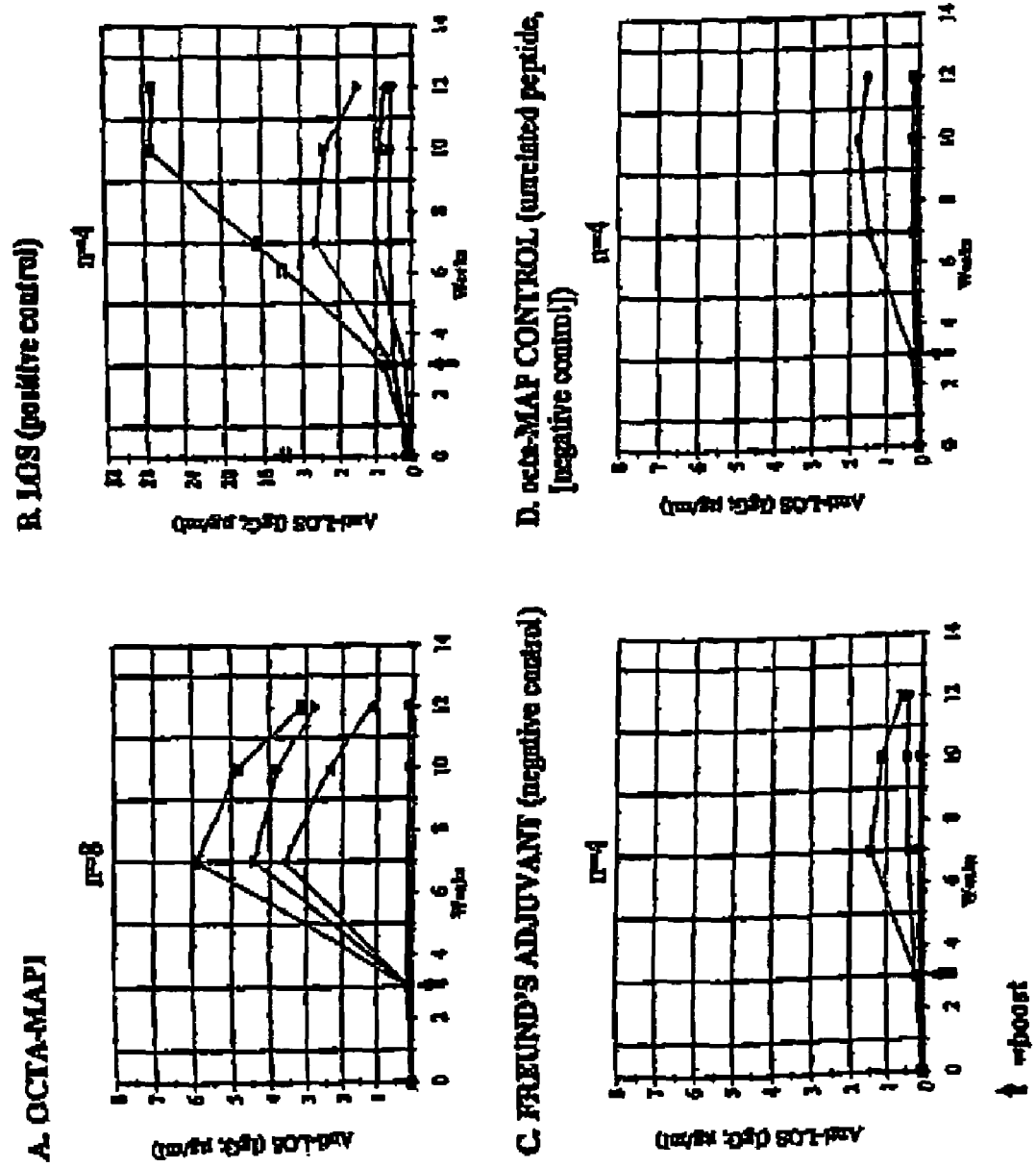
FIGS. 8A–8D show octa-MAP1-induced IgG anti-LOS antibody responses in mice. (A) Eight mice received a dose of 50 μg of Octa-MAP1 emulsified in Freund's adjuvant on day 0 and again on day 21. (B) Four mice were immunized with purified LOS as a positive control. Mice were immunized with either Freund's adjuvant (C) or an unrelated octa-MAP control peptide (D) as negative controls.
Figure 9:
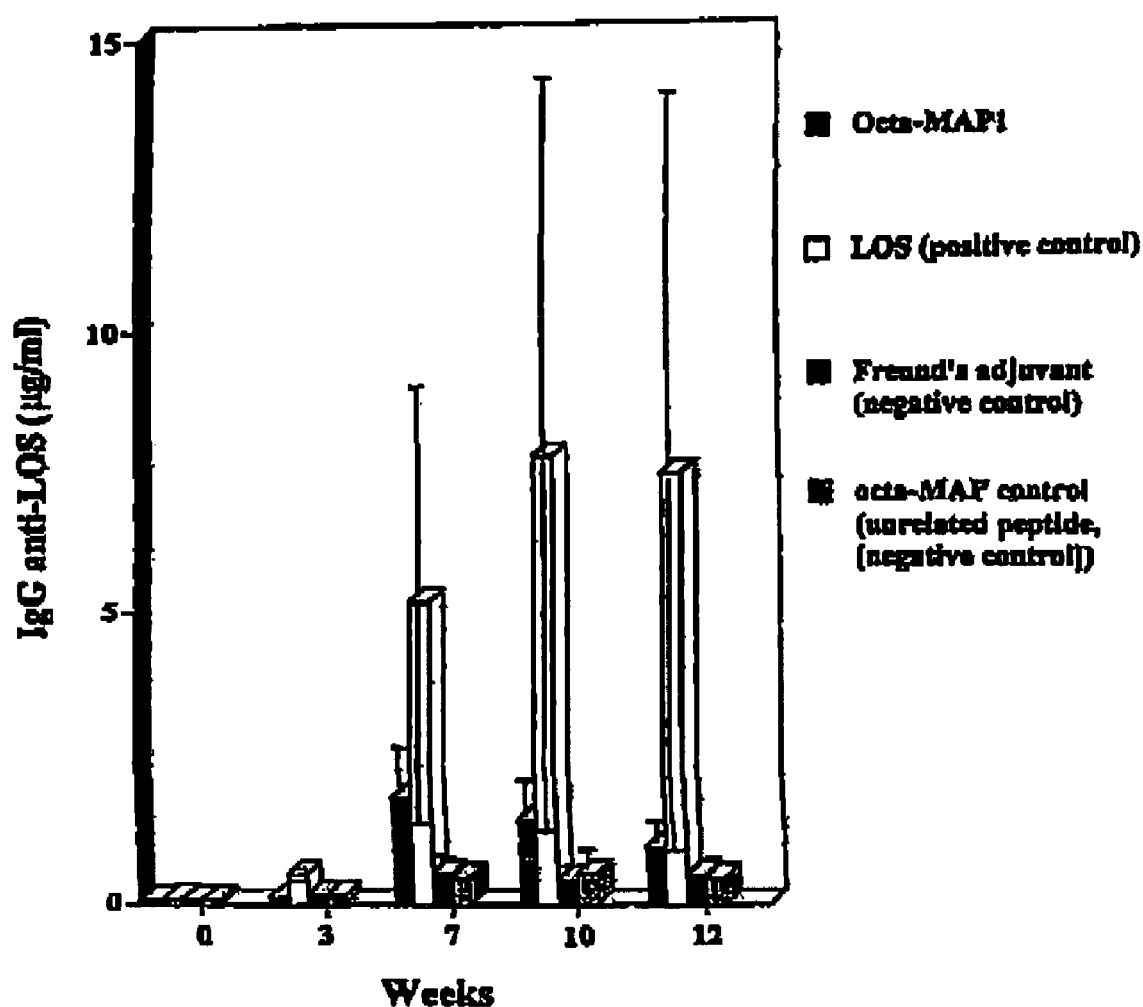
FIG. 9 shows IgG anti-LOS antibody responses in all immunized mice. IgG anti-LOS antibody responses (mean±SE) are shown for all mice (including animals that exhibited no response).

In FIG. 8(A), eight mice received a dose of 50 µg of Octa-MAP1 emulsified in Freund's adjuvant on day 0 and again on day 21. Octa-MAP1, which mimics the 2C7 oligosaccharide epitope, induced IgG anti-LOS antibody in three of the eight mice. IgG anti-LOS responses in these three mice rose significantly after the first boost at week 3, peaked at week 7 (the next time measured) and decreased thereafter. FIG. 8(B) shows the positive control experiment in which four mice were immunized with purified LOS. In these mice, IgG anti-LOS titers increased minimally after the first immunization and rose after boosting. All mice in the LOS group showed an anti-LOS antibody response. Four mice immunized with either Freund's adjuvant (C) or an unrelated octa-MAP control peptide (D), both negative controls, elicited weak or no IgG anti-LOS responses. The mean IgG anti-LOS antibody responses from all immunized mice (from the experiments depicted in FIGS. 8A–8D) are shown in FIG. 9 (mean±SE, including animals that exhibited no response).

Figure 10:
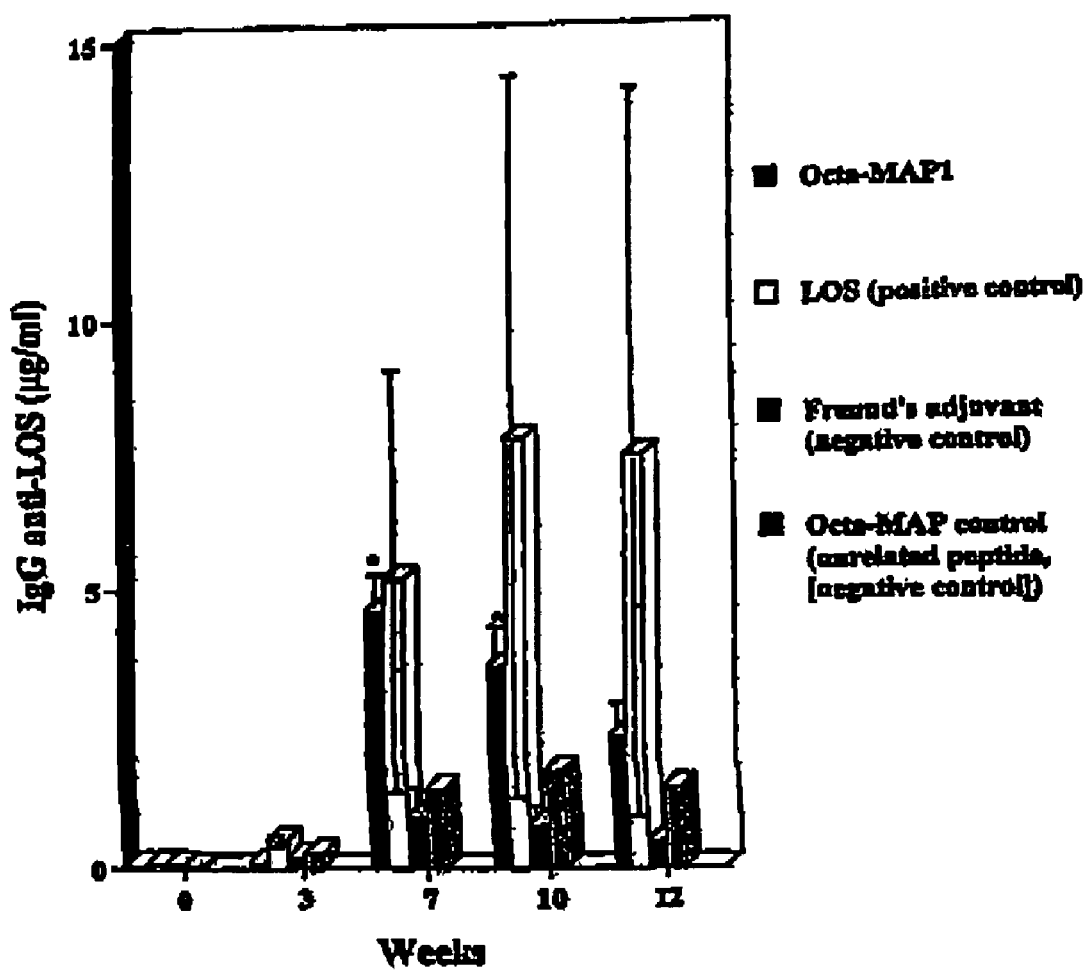
FIG. 10 shows IgG anti-LOS antibody responses in responder mice only. Antibody response was defined as IgG anti-LOS (mean±SE) greater than 0.4 μg/ml (4 fold above baseline IgG anti-LOS levels). Mice were immunized with Octa-MAP1, LOS, Freund's adjuvant alone or unrelated octa-MAP control peptide. Elicited IgG anti-LOS antibody levels were plotted as a function of concentration over time.

IgG anti-LOS antibody responses for the responder mice only (from the experiments depicted in FIGS. 8A–8D) are shown in FIG. 10. Antibody response is defined as IgG anti-LOS (mean±SE) greater than 0.4 mg/ml (4 fold above baseline IgG anti-LOS levels). At 7 and 10 weeks after primary immunization, responder mice immunized with Octa-MAP1 elicited IgG anti-LOS antibody levels higher (p<0.001) than antibody levels elicited by negative control antigens (Freund's adjuvant alone or unrelated octa-MAP control peptide).

Figure 11:
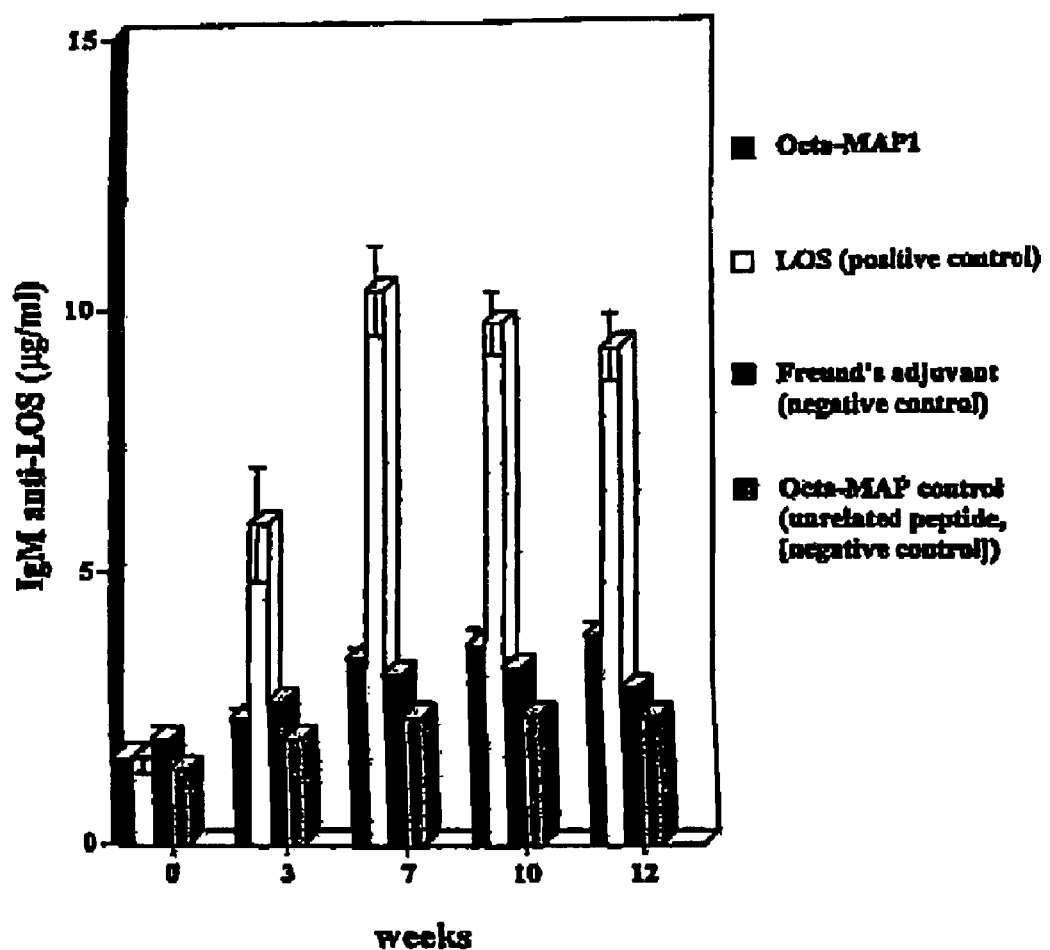
FIG. 11 shows IgM anti-LOS antibody responses in responder mice only. Mice were immunized with Octa-MAP1, LOS, Freund's adjuvant alone or unrelated octa-MAP control peptide. Elicited IgG anti-LOS antibody levels were plotted as a function of concentration over time.

IgM anti-LOS antibody responses for responder mice only (from the experiments depicted in FIGS. 8A–8D) are shown in FIG. 11. Mice immunized with Octa-MAP1 that had elicited IgG anti-LOS responses failed to respond with IgM anti-LOS levels higher than mice immunized with negative control antigens. Immunization with LOS (positive control) elicited IgM anti-LOS antibody levels higher than animals immunized with either Octa-MAP1 or negative control antigens (Freund's adjuvant alone or unrelated octa-MAP control peptide).

Figure 12:
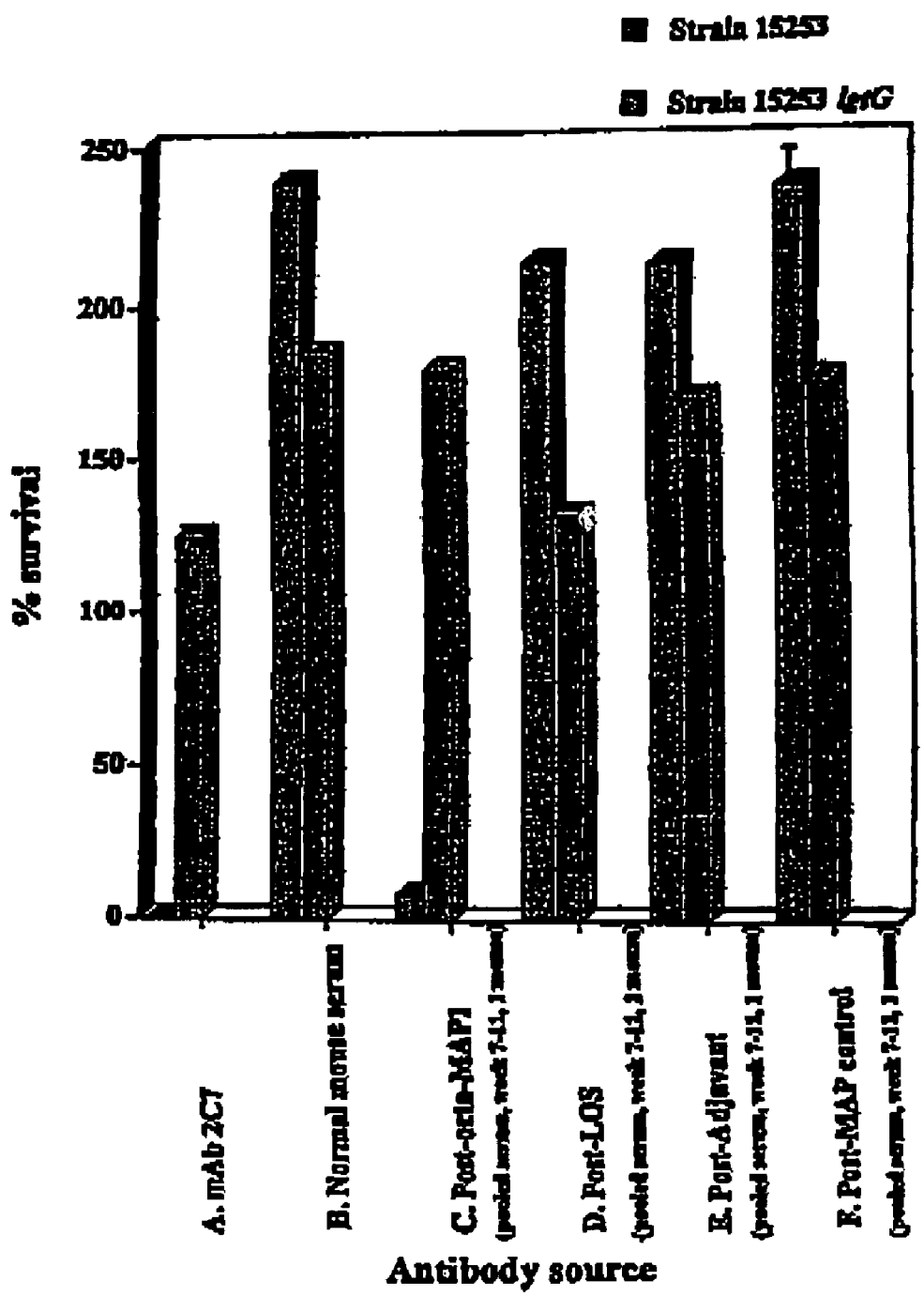
FIG. 12 shows survival of gonorrhoeae strain 15253 and its lgtG mutant (2C7 epitope negative) exposed to mouse immune serum (67% [100 μl of serum in 150 μl total reaction volume] plus added human complement from normal human donor serum [giving a final human complement concentration of 17% by volume]). A bactericidal assay was performed using (A) mAb 2C7 mice against strain 15253 (positive control) and strain 15253 lgtG (negative control) (4). 25 μg/ml of mAb 2C7 (100 μl in 150 μl of total volume of reaction mixture) mediated 100% killing of strain 15253, and no killing of strain 15253 lgtG. (B) Normal mouse serum (pool of 20 mouse sera, mean concentration of IgG anti-LOS antibody, 0.1 μg/ml) failed to kill either strain. (C) Serum taken from a single mouse immunized with Octa-MAP1 (containing 5.05 μg/ml of IgG anti-LOS antibody, pooled from bleeds taken between weeks 7–11) showed 92% killing (8% survival) of strain 15253, whereas strain 15253 lgtG survived fully. (D) Serum taken from a single mouse immunized with LOS (containing 21.98 μg/ml of IgG anti-LOS antibodies, pooled from bleeds taken between weeks 7–11) showed no killing of strain 15253 (179% survival) and strain 15253 lgtG (133% survival). Single mice immunized with negative control antigens (E) Freund's adjuvant alone or (F) unrelated octa-MAP control peptide did not kill either strain.

Serum from a mouse immunized with Octa-MAP1 exhibited 2C7-specific complement-mediated bactericidal activity against $N.$ gonorrhoeae strain 15253, as shown in FIG. 12. Depicted in FIG. 12 is a graph showing survival of $N.$ gonorrhoeae strain 15253 and its lgtG mutant (2C7 epitope negative) (4) exposed to mouse immune serum (67% final mouse immune serum concentration by volume) plus added human complement obtained from normal human donors (17% final human complement concentration by volume).

Strain 15253 exhibits the 2C7 epitope. Strain 15253 lgtG contains a disrupted allele of lipooligosaccharide (LOS) glycosyl transferase G, which transfers glucose (via an ax linkage) onto heptose-2 in the core of LOS (4). The disruption of the lgtG locus results in the loss of 2C7 epitope expression.

A standard bactericidal assay was performed to assess complement-mediated bactericidal activity in mouse sera (11). In this assay, mouse serum (67% final volume) (from various mice immunized or not as described below) was incubated with approximately $2.5 \times 10^3$ bacteria suspended in Morse A media (33) in the presence of human complement (17% final volume). The reaction mixture was then shaken continuously at 37° C. for 30 minutes. Aliquots of the reaction mixture were then inoculated onto chocolate agar plates at time 0 and 30 minutes. Survival was expressed as the percent increase in colonies on the plate at 30 minutes, compared to those on the plate at 0 minutes. Greater than 100% survival in the assay indicates growth during the 30-minute incubation period.

mAb 2C7 was used as a control, as it kills $N.$ gonorrhoeae strain 15253 with added complement, but does not kill the 15253 lgtG mutant strain. As shown in FIG. 12(A), mAb 2C7 possesses bactericidal activity against 2C7 epitope-bearing gonococci. 25 µg/ml of mAb 2C7 (100 µl in 150 µl of total volume of reaction mixture) mediated 100% killing of strain 15253, and no killing of strain 15253 lgtG.

Serum taken from a single mouse immunized with Octa-MAP1, containing 5.05 µg/ml of IgG anti-LOS antibody pooled from bleeds taken between weeks 7–11, showed 92% killing (8% survival) of strain 15253 whereas strain 15253 lgtG survived fully, as depicted in FIG. 12(C).

Normal mouse serum representing a pool of 20 mouse sera with a mean concentration of IgG anti-LOS antibody of 0.1 µg/ml failed to kill either strain, as shown in FIG. 12(B). Control mouse serum without complement showed 116.1%+ 4.7% survival (no killing) for strain 15253, and 123.1%+ 3.5% survival (no killing) for the lgtG mutant of 15253. The complement source without antibody exhibited 137.9%±1.0% survival (no killing) for strain 15253, and 132.5%±4.3% survival (no killing) for the lgtG mutant of 15253.

Serum taken from a single mouse immunized with LOS (containing 21.98 µg/ml of IgG anti-LOS antibodies, pooled from bleeds taken between weeks 7–11) effected no killing of strain 15253 (179% survival) and strain 15253 lgtG (133% survival), as shown in FIG. 12(D). Serum taken from single mice immunized with Freund's adjuvant alone or unrelated Octa-MAP control peptide, as negative control antigens, did not kill either strain, as shown in FIGS. 12(E) and 12(F) respectively.

IgG anti-LOS antisera obtained from mice immunized with Octa-MAP1 exhibited concentration-dependent killing of $N.$ gonorrhoeae strain 15253, as shown in FIG. 13.

FIG. 13 shows a plot of IgG anti-LOS antibody concentration versus killing of $N.$ gonorrhoeae strain 15253. When IgG anti-LOS antisera levels from each of three mice immunized with Octa-MAP1 were plotted against bacterial killing, a dose-response profile resulted (mouse sera containing 1.38, 2.50 and 5.05 µg/ml of anti-LOS antibodies showed 31, 74 and 92% killing, respectively, of strain 15253). Killing by mAb 2C7 was also shown at 5 separate LOS antibody concentrations as a positive control.

B. Coupling a Peptide Mimic to Complement Protein C3d

It is expected that the immunogenicity of peptide mimics of gonococcal epitopes, such as Octa-MAP1 described herein, can be further enhanced through coupling with complement factor C3d.

Numerous studies have demonstrated an important role of complement protein C3 in the induction of humoral immune responses (1, 5, 14, 17, 25, 32, 34 and 35). C3-depleted mice show diminished antibody responses to T-cell dependent protein antigen, such as keyhole limpet haemocyanin ("KLH") (34, 35). Complement receptor 1-(CR1 or CD35) and complement receptor 2-(CR2 or CD21) deficient mice have an impaired T-cell dependent antibody response (1, 14, 32). It has further been shown that C3d covalently linked to hen egg lysozyme ("HEL") resulted in an enhanced antibody response to the HEL antigen (15). Mice immunized with a fusion protein that consisted of three copies of C3d and 1 copy of HEL elicited a 10,000-fold increase in anti-HEL antibody response, compared to antibody responses in mice immunized with HEL alone. Anti-HEL antibody responses induced by the fusion protein were approximately 100-fold higher than those induced by HEL emulsified in Freund's adjuvant.

Octa-MAP1 can be coupled to C3d by cloning an octa-MAP1 DNA sequence into a C3d fusion protein cassette and transforming this construct into an expression system. The OctaMAP1-C3d fusion protein can then be expressed, purified and used as an immunogen. Alternatively, the OctaMAP1-C3d gene fusion, in the form of DNA, can be used as a DNA vaccine according to methods known in the art.

A hybridoma producing anti-idiotypic antibodies exhibiting immunological reactivity similar to the peptide mimics of the instant invention is exemplified by a cell culture deposited in the ATCC (10801 University Boulevard, Manassas, Va. 20110-2209 U.S.A.) on Mar. 26, 1993 and assigned ATCC accession number HB 11311.

Hybridoma 2C7 secreting the mAb 2C7 exhibiting immunological reactivity similar to the peptide mimics of the instant invention is exemplified by a cell culture designated as 2C7 and deposited in the ATCC on Mar. 9, 1995. This culture was assigned ATCC accession number HB-11859.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

LITERATURE CITED

1. Ahearn, J. M., M. B. Fischer, D. Croix, S. Goerg, M. Ma, J. Xia, X. Zhou, R. G. Howard, T. L. Rothstein, and M. C. Carroll. 1996. Disruption of the Cr2 locus results in a reduction in B-1a cells and in an impaired B cell response to T-dependent antigen. Immunity 4:251.
2. Apicella, M. A., M. A. Westerink, S. A. Morse, H. Schneider, P. A. Rice and J. M. Griffiss. 1986. Bactericidal antibody response of normal human serum to the lipooligosaccharide *Neisseria gonorrhoeae*. J. Infect. Dis. 153: 520–526.
3. Arnon, R., M. Shapira and C. O. Jacob. 1983. Synthetic Vaccines. J. Immunol. Methods 61: 261–273.
4. Banerjee A., R. Wang, S. N. Uljon, P. A. Rice, and E. C. Gotschlich. 1998. Identification of the gene (lgtG) encoding the lipooligosaccharide β chain synthesizing glucosyl transferase from *Neisseria gonorrhoeae*. Proc. Natl. Acad. Sci. USA 95:10872.
5. Böttger, E. C., and D. Bitter-Suermann. 1987. Complement and the regulation of humoral immune responses. Immunol. Today 8:261.
6. Britigan, B. E., M. S. Cohen and P. F. Sparling. 1985. Gonococcal infection: a model of molecular pathogenesis. N. Eng. J. Med. 312: 1683–1694.
7. Brooks, G. F. and C. J. Lammel. 1989. Humoral immune response to gonococcal infection. Chn. Micro. Rev. 2S: S5-S 10.
8. Burritt, J. B., C. W. Bond, K. W. Doss and A. J. Jesiatis. 1996. Filamentous phage display of oligopeptide libraries. Anal. Biochem. 338: 1–13.
9. CDC/NIH Workshop on pelvic inflammatory disease: Prevention, Management and Research Directions in the 1990's. September 1990.
10. CDC. 1982. Sexually transmitted diseases treatment guidelines. MMWR. 31: Suppl. 2: S37S42.
11. CDC. 1984. Chromosomally mediated resistant *Neisseria gonorrhoeae*—United States. MMWR. 33: 408–410.
12. CDC Website. 2000.

http://www.cdc.gov/ncidod/dastlr/qcdir/Resist/gisp.html

13. Cohen, I. R., D. S. Kellogg and L. C. Norins. 1969. Serum antibody response in experimental human *gonorrhoeae*: immunoglobulins G, A and M. Br. J. Ven. Dis. 45: 325–327.
14. Croix, D. A., J. M. Ahearn, A. M. Rosengard, S. Han, G. Kelsoe, M. Ma, and M. C. Carroll. 1996. Antibody response to a T-dependent antigen requires B cell expression of complement receptors. J. Exp. Med. 183:1857.
15. Dempsey, P. W., M. E. D. Allison, S. Akkaraju, C. C. Goodnow, and D. T. Fearon. 1996 C3d of complement as a molecular adjuvant: Bridging innate and acquired immunity. Sciences 271: 348.
16. Densen, P., S. Gulati and P. A. Rice. 1987. Specificity of antibodies against *Neisseria gonorrhoeae* that stimulate neutrophil chemotaxis. J. Clin. Invest. 80: 78–87.
17. Fischer, M. B., M. Ma, S. Goerg, X. Zhou, J. Xia, X. Zhou, R. G. Howard, T. L. Rothstein, E. Kremmer, F. S. Rosen, and M. C. Carroll. 1996. Regulation of the B cell response to T-dependent antigens by classical Pathway complement. J. Immunol. 157:549.
18. Glynn, A. A. and M. E. Ward. 1970. Nature and heterogeneity of the antigens of *Neisseria gonorrhoeae* involved in the bactericidal reaction. Infect. Immun. 2: 162–168.
19. Griffiss, H. M., J. P. O'Brien, R. Yamasaki, G. D. Williams, P. A. Rice and H. Schneider. 1987. Physical heterogeneity of Neisserial lipooligosaccharides reflects oligosaccharides that differ in apparent molecular weight, chemical composition, and antigenic expression. Infect. Immun. 55: 1792–1800.
20. Gulati, S., D. P. McQuillen, J. Sharon, and P. A. Rice. 1996. Experimental Immunization with a Monoclonal Anti-Idiotope Antibody that Mimics the *Neisseria gonorrhoeae* Lipooligosaccharide Epitope 2C7. J. Infect. Dis. 174: 1238–48.
21. Gupta, R. K. and G. R. Siber. 1995. Adjuvants for human vaccines—current status, problems and future prospects. Vaccine 13: 1263–1276.
22. Gupta, R. K. and G. R. Siber. 1995. Method for quantitation of IgG subclass antibodies in mouse serum by enzyme-linked immunosorbent assay. J. Immunol. Methods 181: 75–81.
23. Jerne, N. K. 1974. Towards a network theory of the immune system. Ann. Inst. Pasteur. Immun. 125C: 373–389.
24. Kieber-Emmons T. 1998. Peptide mimotopes of carbohydrate antigens. Immunol. Res. 17: 95–108.
25. Klaus G. G. B., and J. H. Humphrey. 1977. The generation of memory cells I. The role of C3 in the generation of B memory cells. Immunology 33:31.
26. Lambden, P. R., J. E. Heckels, H. McBride and P. J. Watt. 1981. The identification and isolation of novel pilus types produced by variants of *Neisseria gonorrhoeae* P9 following selection in vivo. FEMS. Microbiol. Lett. 10: 339–341.
27. Lammel, C. J., R. L. Sweet, P. A. Rice, J. S. Knapp, G. K. Schoolnik, D. C. Heilbron and G. F. Brooks. 1985. Antibody-antigen specificity in the immune response to infection with *Neisseria gonorrhoeae*. J. Infect. Dis. 152: 990–1001.
28. Lowell, G. H., W. R. Ballou, L. F. Smith, R. A. Wirtz, W. D. Zollinger and W. T. Hockmeyer. 1988. Proteosome-lipopeptide vaccines: enhancement of immunogenicity for malaria CS peptides. Science 240: 800–802.
29. Luo P., M. Agadjanyan, J. Qiu, M. A. Westerink, Z. Steplewski and T. Kieber-Emmons. 1998. Antigenic and immunological mimicry of peptide mimotopes of Lewis carbohydrate antigens. Mol. Immunol. 35: 865–879.
30. Mandrell, R. E., H. Schneider, M. A. Apicella, W. D. Zollinger, P. A. Rice and J. M. Griffiss. 1986. Antigenic and physical diversity of *Neisseria gonorrhoeae* lipooligosaccharides. Infect. Immun. 54: 63–69.
31. McQuillen D. P., S. Gulati, and P. A. Rice. 1994. Complement-mediated bacterial killing assays. Methods Enzymol. 236: 137.
32. Molina, H., V. M. Holers, B. Li, Y.-F. Fang, S. Mariathasan, J. Goellner, J. Strauss-Schoenberger, R. W. Karr, and D. D. Chaplin. 1996. Markedly impaired humoral response in mice deficient in complement receptors 1 and 2. Proc. Natl. Acad. Sci. USA 93:3357.
33. Morse S. A., S. Stein and J. Hines. 1974. Glucose metabolism in *Neisseria gonorrhoeae*. J. Bact. 120: 702.

34. Pepys M. B. 1972. Role of complement in induction of the allergic response. Nature [New Biol] 273: 157.
35. Pepys, M. B. 1974. Role of complement in induction of antibody production in vivo. J. Exp. Med. 140:126.
36. Rice, P. A. and D. L. Kasper. 1977. Characterization of gonococcal antigens responsible for gonococcal bactericidal antibody in disseminated infection. J. Clin. Invest. 60: 1149–1158.
37. Rice, P. A. and D. L. Kasper. 1982. Characterization of serum resistance of *Neisseria gonorrhoeae* that disseminate. J. Clin. Invest. 70: 157–167.
38. Roberts, R. B. 1967. The interaction in vitro between Group B meningococci and rabbit polymorphonuclear leukocytes. J. Exp. Med. 126: 795–817.
39. Romero, P. J., J. P. Tam, D. Schlesinger, P. Clavijo, P. J. Barr, R. S. Nussenzweig, V. Nussenzweig and F. Zavala. 1988. Multiple T helper cell epitopes of the circumsporozoite protein of *Plasmodium berghei*. Eur. J. Immunol. 18: 1951–1957.
40. Schaaper, W. M., Lu, Y. A., Tam, J. P. and R. H. Meloen. 1990. p. 765. In: Peptides: Chemistry, Structure and Biology. Rivier, I. E. and G. R. Marshall (eds.). ESCOM Science Publishers, Leiden.
41. Schoolnik, G. K. and Z. A. McGee. 1985. Gonococcal vaccine development strategies: summary of the recommendations of a National Institutes of Health vaccine panel. p. 329–331. In: G. K. Schoolnik, G. F. Brooks, S. Falkow, C. E. Frasch, J. S. Knapp, J. A. McCutchan and S. A. Morse. (ed.). The pathogenic *Neisseria*. ASM. Washington D. C.
42. Schreiber, J. R., M. Patarawan, M. Tosi, J. Lennon and G. B. Pier. 1990. Anti-idiotype-induced lipo-oligosaccharide specific Antibody response to *Pseudomonas aeroginosa*. J. Immun. 144: 1023–1029.
43. Shinnick, T. M., J. G. Sutcliff, N. Green and R. Lerner. 1983. Synthetic peptide immunogens as vaccines. Annu. Rev. Microbiol. 37: 425–446.
44. Smith, G. P. and J. K. Scott. 1993. Libraries of peptides and proteins displayed on filamentous phage. Methods Enzymol. 217: 228–257.
45. Swanson, J. 1982. Colony opacity and protein II composition of gonococci. Infect. Immun. 37: 359–368.
46. Tramont, E. C., J. C. Sadoff and M. S. Artenstein. 1974. Cross reactivity of *Neisseria gonorrhoeae* and *Neisseria meningitidis* and the nature of antigens involved in the bactericidal reaction. J. Infect. Dis. 130: 240–247.
47. Tramont, E. C. and J. Ciak. 1978. Antigonococcal antibodies in genital secretions. p. 274–278. In: G. F. Brooks, E. C. Gotschlich, W. D. Sawyer and F. E. Young (ed.). lmmunobiology of *Neisseria gonorrhoeae*. Washington D.C. ASM.
48. Tramont, E. C., J. W. Boslego, R. Chung, D. McChesney, J. Ciak, J. Sadoff, M. Piziak, C. C. Brinton, S. Wood and J. Bryan. 1985. Parenteral gonococcal pilus vaccine. p. 316–322. In: G. K. Schoolnik, G. F. Brooks, S. Falkow, C. E. Frasch, J. S. Knapp, J. A. McCutchan and S. A. Morse. (eds.). The pathogenic *Neisseria*. Washington D.C. ASM.
49. Tramont, E. C. 1989. Gonococcal vaccines. Clin. Micro. Rev. 2S: S74–S77.
50. Ward, E. S., D. Güssow, A. D. Griffiths, P. T. Jones and G. Winter. 1989. Binding activities of a repertoire of a single immunoglobulin variable domains secreted from *Escherichia coli*. Nature 341: 544–546.
51. Ward, M. E., P. R. Lambden, J. E. Heckels and P. J. Ward. 1978. The surface properties of *Neisseria gonorrhoeae*: determinants of susceptibility to antibody complement killing. J. Gen. Micro. 108: 205–212.
52. Ward, M. M., R. E. Ward, J. H. Huang and H. Kohler. 1984. Idiotope Vaccine Against *Streptococcus pneumonia*. A precursor study. J. Immunol. 1 39: 2775–2780.
53. Washington, A. E. 1982. Update on treatment recommendations for gonococcal infections. Rev. Infect. Dis. 4S: S758–S771.
54. Westerink, M. A., P. C. Giardina, M. A. Apicella and T. Kieber-Emmons. 1995. Peptide mimicry of the meningococcal group C capsular polysaccharide. Proc. Natl. Acad. Sci. USA. 92: 4021–4025.
55. Zavala, F., J. P. Tam, M. R. Hollingdale, A. H. Cochrane, I. Quakyi, R. S. Nussenzweig and V. Nussenzweig. 1985. Rationale for development of a synthetic vaccine against *Plasmodium falciparum* malaria. Science 228: 1436–1440.

We claim:

1. An isolated peptide mimic of a conserved gonococcal lipo-oligosaccharide (LOS) epitope not found on human blood group antigens, wherein said peptide mimic is capable of inducing in a mammal an immune response against said conserved gonococcal lipo-oligosaccharide (LOS) epitope and wherein said peptide mimic comprises the amino acid sequence of SEQ ID NO:1.

2. The peptide mimic according to claim 1, wherein the immune response is T-cell dependent.

3. The peptide mimic according to claim 1, wherein the amino acid sequence of the peptide mimic comprises cysteine residues at each terminus.

4. The peptide mimic according to claim 3, wherein a cyclic peptide is formed through disulfide bridges between the cysteine residues at each terminus of said amino acid sequence.

5. The peptide mimic according to claim 4, wherein the peptide mimic is coupled to a second agent.

6. The peptide mimic according to claim 5, wherein the second agent is an adjuvant.

7. The peptide mimic according to claim 1, wherein the peptide mimic further comprises an adjuvant or a carrier protein.

8. The peptide mimic according to claim 1, wherein the peptide mimic is part of a multiple-antigen peptide (MAP).

9. The peptide mimic according to claim 1, wherein said peptide mimic competes with gonococcal lipooligosaccharide (LOS) for binding to monoclonal antibody 2C7 produced by a hybridoma cell line having the ATCC accession number HB-11859.

10. The peptide mimic according to claim 1, wherein the peptide mimic immunospecifically binds to monoclonal antibody 2C7 produced by a hybridoma cell line having the ATCC accession number HB-11859.

11. The peptide mimic according to claim 1, wherein the peptide mimic immunospecifically binds to a monoclonal antibody produced by immunizing a mammal with an anti-idiotypic monoclonal antibody, or fragment thereof, wherein said anti-idiotypic monoclonal antibody is produced by a hybridoma cell line having the ATCC accession number HB-11311.

12. A composition for immunizing against *N. gonorrhoeae* infection comprising an immunoprophylactically effective amount of the peptide mimic according to any one of claims 1, 2, 4–6, 10 and 11.

13. A composition for immunizing against *N. gonorrhoeae* infection comprising an immunoprophylactically effective amount of an isolated peptide mimic comprising the amino acid sequence of SEQ ID NO: 1.

14. A method of immunizing a mammal against *N. gonorrhoeae* infection comprising administering to said mammal an immunoprophylactically effective amount of the peptide mimic according to claim 1 or claim 2 and a pharmaceutically acceptable carrier.

15. A method of immunizing a mammal against *N. gonorrhoeae* infection comprising administering to said mammal an immunoprophylactically effective amount of the peptide mimic according to claim 10 or claim 11 and a pharmaceutically acceptable carrier.

16. The peptide mimic according to claim 1, wherein the peptide mimic is coupled to a complement protein.

17. The peptide mimic according to claim 16, wherein the complement protein is C3d.

18. A method of immunizing a mammal against *N. gonorrhoeae* infection comprising administering to said mammal an immunoprophylactically effective amount of the peptide mimic according to claim 17 and a pharmaceutically acceptable carrier.

19. A composition for immunizing against *N. gonorrhoeae* infection comprising an immunoprophylactically effective amount of the peptide mimic according to claim 17.

20. A method for increasing the antigenicity of the peptide mimic according to claim 1 comprising coupling said peptide mimic to a complement protein.

21. The method according to claim 20, wherein the complement protein is C3d.

* * * * *

UNITED STATES PATENT AND TRADEMARK OFFICE
CERTIFICATE OF CORRECTION

| | | |
|---|---|---|
| PATENT NO. | : 7,189,405 B1 | Page 1 of 1 |
| APPLICATION NO. | : 09/699224 | |
| DATED | : March 13, 2007 | |
| INVENTOR(S) | : Peter A. Rice et al. | |

It is certified that error appears in the above-identified patent and that said Letters Patent is hereby corrected as shown below:

In the Specification

At column 1, line 9, insert the following paragraph:

--FEDERALLY SPONSORED RESEARCH

This invention was made with government support under grant number AI032725 awarded by the National Institutes of Health. The government has certain rights in the invention.--

Signed and Sealed this
First Day of March, 2016

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Ile Pro Val Leu Asp Glu Asn Gly Leu Phe Ala Pro
  1               5                  10

<210> SEQ ID NO 2
<211> LENGTH: 12
<212> TYPE: PRT
<213> ORGANISM: Artificial Sequence
<220> FEATURE:
```

-continued

<223> OTHER INFORMATION: Description of Artificial Sequence: Synthetic
      construct

<400> SEQUENCE: 2

Trp Gly Leu Asp Tyr Glu Arg Gly Asn Tyr Glu Glu
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Asp Ala Leu Ala Val Asp Gln Met Gly Arg Phe Gly
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Val Leu Val Gly Glu Lys Gly Leu Phe Glu Gly Gly
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Glu Ala Leu Val Leu Asp Thr Asn Gly Leu Met Ser
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Ala Asp Arg Thr Gln Gly Leu Gly Trp Gly Ala Ser
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Glu Glu Val Gly Ser Ile Leu Tyr Gly Leu Gly Gly
 1               5                  10

-continued

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (3)
<223> OTHER INFORMATION: Any amino acid

<400> SEQUENCE: 8

Asp Glu Xaa Gly Leu Phe
 1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9

Cys Lys Ser Asn Pro Ile His Ile Ile Lys Asn Arg Arg Asn Ile Pro
 1               5                  10                  15

Cys

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Cys Gly Pro Ile Pro Val Leu Glu Asn Gly Leu Phe Gly Pro Cys
 1               5                  10                  15
```